United States Patent [19]
Gruenert et al.

[11] Patent Number: 5,804,383
[45] Date of Patent: Sep. 8, 1998

[54] METHOD AND ASSAY FOR DETECTION OF THE EXPRESSION OF ALLELE-SPECIFIC MUTATIONS BY ALLELE-SPECIFIC IN SITU REVERSE TRANSCRIPTASE POLYMERASE CHAIN REACTION

[75] Inventors: Dieter C. Gruenert, Mill Valley; Austin F. Dohrman, San Francisco, both of Calif.

[73] Assignee: The Regents of the University of California, Oakland, Calif.

[21] Appl. No.: 727,003

[22] Filed: Oct. 8, 1996

Related U.S. Application Data

[60] Provisional application No. 60/005,254 Oct. 10, 1995.

Related U.S. Application Data

[63] Continuation-in-part of Ser. No. 487,799, Jun. 7, 1995, which is a continuation-in-part of Ser. No. 409,544, Mar. 24, 1995, abandoned, which is a continuation of Ser. No. 933,471, Aug. 21, 1992, abandoned.

[51] Int. Cl.⁶ .............................. C12Q 1/68; C12P 19/34
[52] U.S. Cl. .............................. 435/6; 435/40.5; 435/91.2
[58] Field of Search .............................. 435/6, 40.5, 91.2; 536/24.33

[56] References Cited

FOREIGN PATENT DOCUMENTS

WO 94/04032  3/1994  WIPO .

OTHER PUBLICATIONS

I.A. Teo and S. Shaunak, PCR in situ: aspects which reduce amplification and generate false–positive results, *Histochemcial Journal*, 27:660–669, (1995).

Alfredo Martinez, Mae–Jean Miller, Kathryn Quinn, kEdward J. Unsworth, Masahito Ebina and Frank Cuttitta, Non–radioactive Localization of Nucleic Acids by Direct In Situ PCR and In Situ RT–PCR in Paraffin–embedded Sections, *The Histochem. Cytochem.*, 43: (8):739–746, (1995).
I. A. Teo and S. Shaunak, Polymerase chain reaction in situ: an appraisal of an emerging technique, *Biochemical Journal*, 27:647–659, (1995).
Gerard Nuovo, In Situ RT–PCR Detection of Gelatinase mRNA in HeLa Cells on the GeneAmp In Situ PCR System 1000, *Research News*, 1–5, (Mar. 1995).
Gerard Nuovo, M.D., RT In Situ with Direct Incorporation of Digoxigenin–11–dUTP: Protocol and Applications, *Biochemica*, 11, 1:4–61, (Winter 1994).
Staecker, M. Cammer, R. Rubinstein, T.R. Van De Water, A Procedure for RT–PCR Amplification of mRNAs on Histological Specimens, *BioTechniques*, 16:76–80 (1994).
Rosenfeld et al. (1992) In vivo transfer of the human cystic fibrosis transmembrane conductance regulator gene to the airway epithelium. Cell 68:143–155, Jan. 1992.

*Primary Examiner*—George C. Elliott
*Assistant Examiner*—Robert Schwartzman
*Attorney, Agent, or Firm*—Hana Verny

[57] ABSTRACT

A method and an allele-specific in situ reverse transcriptase polymerase chain reaction (RT-PCR) amplification assay for detection and differentiation between expression of unmutated wild-type DNA sequences and between endogenous mutated DNA sequences in vitro or in vivo. The method is useful for verification, diagnostic assessment and monitoring of therapeutic small fragment homologous replacement gene therapy, for diagnostic assessment and monitoring of cDNA-based gene therapies, for analysis of gene expression of specific alleles during fetal development and for diagnostic assessment of the expression of alleles involved in cancer mutations.

9 Claims, 14 Drawing Sheets

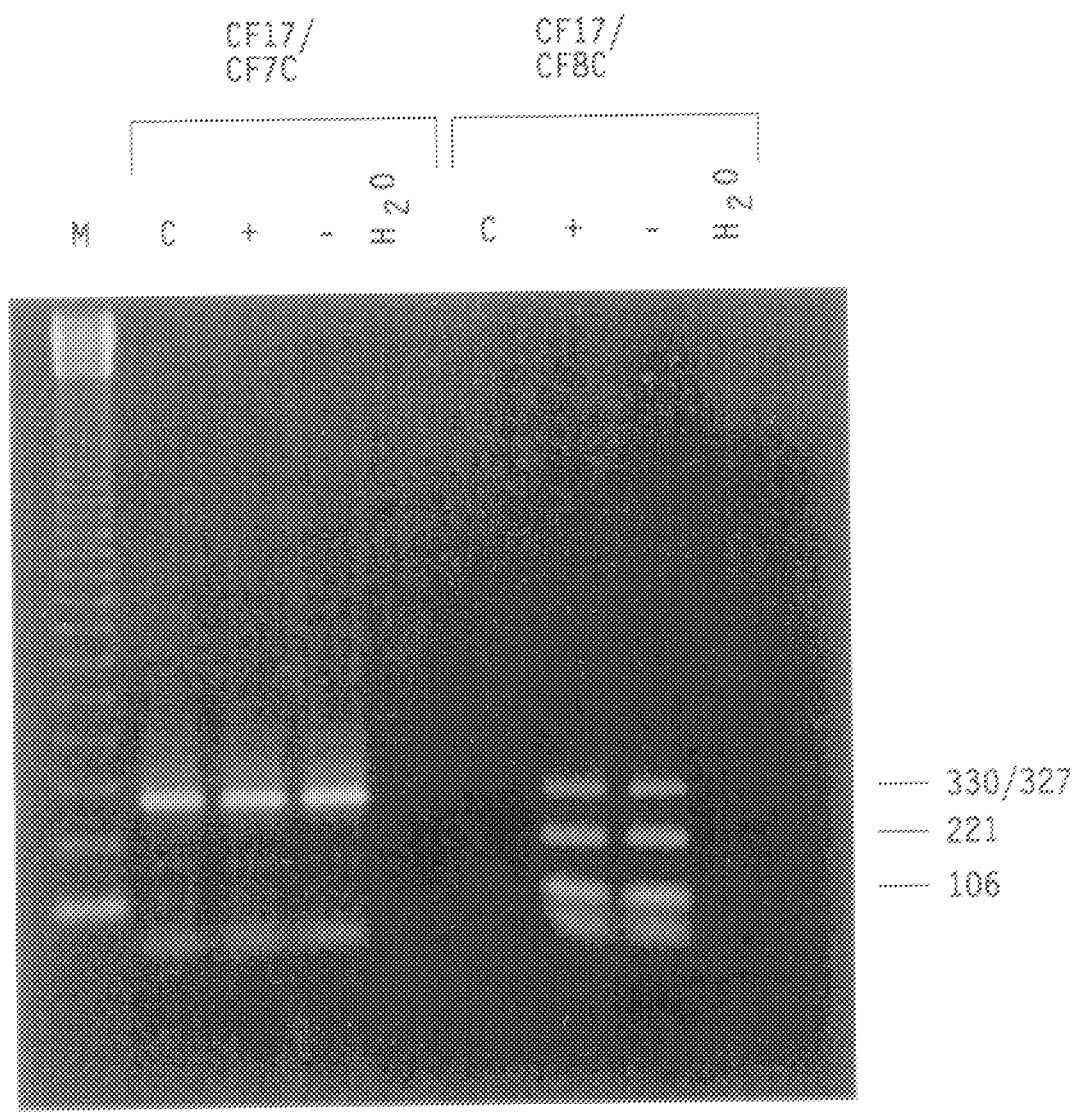

PCR Analysis HU β-Globin DNA

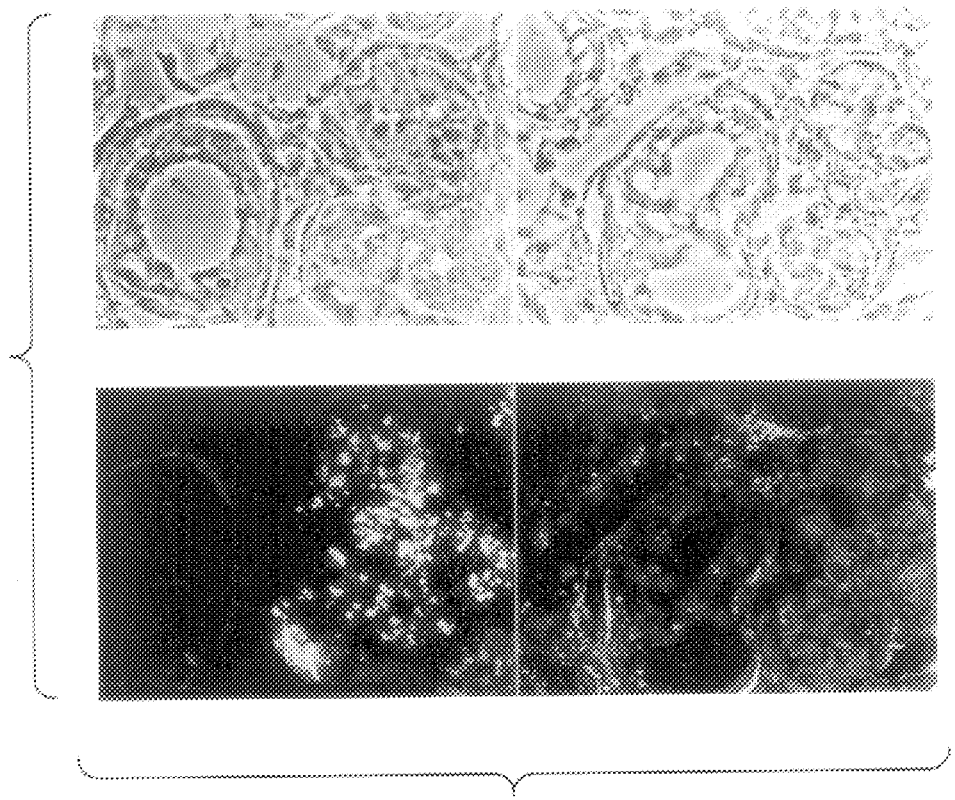
FIG. 11A
FIG. 11B
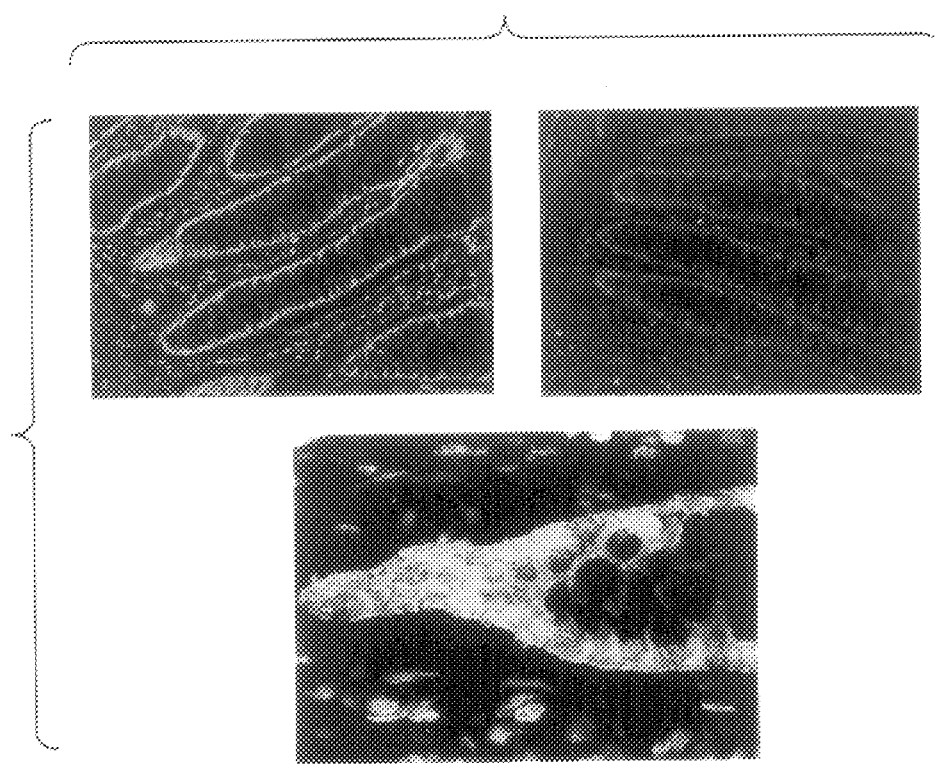

SEQUENCE LISTING ( 1 ) GENERAL INFORMATION:

( i i i ) NUMBER OF SEQUENCES:55

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 1:

GCAGAGTACC TGAAACAGGA					20

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 2:

CCTTCTCTGT GAACCTCTAT CA					22

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 3:

CATTCACAGT AGCTTACCCA					20

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 4:

CCACATATCA CTATATGCAT GC					22

( 2 ) INFORMATION FOR SEQ ID NO:5:

( i ) SEQUENCE CHARACTERISTICS:
        ( A ) LENGTH: 22 base pairs
        ( B ) TYPE: nucleic acid (C) STRANDEDNESS: single
            (D) TOPOLOGY: linear (i i) MOLECULE TYPE: synthetic oligonucleotide (i i i) SEQUENCE DESCRIPTION: SEQ ID NO: 5:

CCATTAAAGA AAATATCATT GG                                                                  22

(2) INFORMATION FOR SEQ ID NO:6:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (i i) MOLECULE TYPE: synthetic oligonucleotide (i i i) SEQUENCE DESCRIPTION: SEQ ID NO: 6:

CCATTAAAGA AAATATCATT GG                                                                  22

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (i i) MOLECULE TYPE: synthetic oligonucleotide (i i i) SEQUENCE DESCRIPTION: SEQ ID NO: 7:

ATAGGAAACA CCAAAGATGA                                                                     20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (i i) MOLECULE TYPE: synthetic oligonucleotide (i i i) SEQUENCE DESCRIPTION: SEQ ID NO: 8:

ATAGGAAACA CCAATGATAT                                                                     20

(2) INFORMATION FOR SEQ ID NO:9:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (i i) MOLECULE TYPE: synthetic oligonucleotide (i i i) SEQUENCE DESCRIPTION: SEQ ID NO: 9:

ACTTTAAAGC TGTCAAGCCG TG                                                                  22

(2) INFORMATION FOR SEQ ID NO:10:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (i i) MOLECULE TYPE: synthetic oligonucleotide ( i i i ) SEQUENCE DESCRIPTION: SEQ ID NO: 10:

CTGTATTTTG TTTATTGCTC CAA 23

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 11:

GAGGGATTTG GGGAATTATT TG 22

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 12:

CTTGCTAAAG AAATTCTTGC TC 22

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 13:

CACCAAAGAT GATATTTTC 19

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 14:

AACACCAATG ATATTTTCTT 20

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 15:

CTTTTCCTGG ATTATGCCTG GCAC 24

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 16:

TAGCAATTTG TACTGATGGT ATG      23

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 17:

TATACACAAT TTAAGGCATT AG      22

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 18:

CCCTGTGGAG CCACACCCTA GGGT      24

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 19:

AACGATCCTG AGACTTCCAC ACT      23

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 20:

ACATTTGCTT CTGACACAAC TGTG      24

( 2 ) INFORMATION FOR SEQ ID NO:21:

( i ) SEQUENCE CHARACTERISTICS:
        ( A ) LENGTH: 23 base pairs
        ( B ) TYPE: nucleic acid ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 21:

AGGGTTGCCC ATAACAGCAT CAG 23

( 2 ) INFORMATION FOR SEQ ID NO:22:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 22:

CTTCTCCTCA GGAGT 15

( 2 ) INFORMATION FOR SEQ ID NO:23:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 23:

CTTCTCCACA GGAGT 15

( 2 ) INFORMATION FOR SEQ ID NO:24:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 24:

AGCATTTTTC AGGTTCCTCC AG 22

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 25:

AACCTACTTA ACCTGGCTTC CT 22

( 2 ) INFORMATION FOR SEQ ID NO:26:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 26:

GGCTTGTTTT GAAGTTACAG GC 22

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 27:

AAGCCATCAG CAACCACAAG A 21

( 2 ) INFORMATION FOR SEQ ID NO:28:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 28:

CCTCATCACT AATCACACTT TG 22

( 2 ) INFORMATION FOR SEQ ID NO:29:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 29:

TCCTCATCAC TAATCACACT TG 22

( 2 ) INFORMATION FOR SEQ ID NO:30:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 30:

GAAGTTTCAT TGAAGTGCAA AG 22

( 2 ) INFORMATION FOR SEQ ID NO:31:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 31:

GGAAGTTTCA TTGAAGTGCA AG 22

( 2 ) INFORMATION FOR SEQ ID NO:32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 32:

GCAGAGTACC TGAAACAGGA AGTA     24

( 2 ) INFORMATION FOR SEQ ID NO:33:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 33:

CTTGTCACAC TGTATTGTAA TTG     23

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 34:

GTAAGTGTCA TCGAATGGGT     20

( 2 ) INFORMATION FOR SEQ ID NO:35:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 35:

CATTCACAGT AGCTTACCCA TAGA     24

( 2 ) INFORMATION FOR SEQ ID NO:36:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 36:

GTAAGTGTCA TCGAATGGGT ATCT     24

( 2 ) INFORMATION FOR SEQ ID NO:37:

( i ) SEQUENCE CHARACTERISTICS:
        ( A ) LENGTH: 22 base pairs
        ( B ) TYPE: nucleic acid (C) STRANDEDNESS: single
(D) TOPOLOGY: linear (ii) MOLECULE TYPE: synthetic oligonucleotide (iii) SEQUENCE DESCRIPTION: SEQ ID NO: 37:

GGTGTATAGT GATATACGTA CG  22

(2) INFORMATION FOR SEQ ID NO:38:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: synthetic oligonucleotide (iii) SEQUENCE DESCRIPTION: SEQ ID NO: 38:

AGAAAATATC ATCTTTGG  18

(2) INFORMATION FOR SEQ ID NO:39:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: synthetic oligonucleotide (iii) SEQUENCE DESCRIPTION: SEQ ID NO: 39:

TATCCTTTGT GGTTTCTACT  20

(2) INFORMATION FOR SEQ ID NO:40:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: synthetic oligonucleotide (iii) SEQUENCE DESCRIPTION: SEQ ID NO: 40:

AGAAAATATC ATTGGTGT  18

(2) INFORMATION FOR SEQ ID NO:41:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: synthetic oligonucleotide (iii) SEQUENCE DESCRIPTION: SEQ ID NO: 41:

ATAGGAAACA CCAATGATAT  20

(2) INFORMATION FOR SEQ ID NO:42:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: synthetic oligonucleotide ( i i i ) SEQUENCE DESCRIPTION: SEQ ID NO: 42:

TATCCTTTGT GGTTACTATA 20

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 43:

GTTTTCCTGG ATTATGCCTG GCAC 24

( 2 ) INFORMATION FOR SEQ ID NO:44:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 44:

GTTGGCATGC TTTGATGACG CTTC 24

( 2 ) INFORMATION FOR SEQ ID NO:45:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 45:

CAACCGTACG AAACTACTGC GAAG 24

( 2 ) INFORMATION FOR SEQ ID NO:46:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 46:

GAACGATTTC TTTAAGAACG AG 22

( 2 ) INFORMATION FOR SEQ ID NO:47:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) SEQUENCE DESCRIPTION: SEQ ID NO: 47:

CTTGTGGGAA ATCCTGTGCT GAA 23

( 2 ) INFORMATION FOR SEQ ID NO:48:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: synthetic oligonucleotide ( i i i ) SEQUENCE DESCRIPTION: SEQ ID NO: 48:

CCTTCTCCAA GAACTGTGTT GTC  23

( 2 ) INFORMATION FOR SEQ ID NO:49:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: synthetic oligonucleotide ( i i i ) SEQUENCE DESCRIPTION: SEQ ID NO: 49:

GGCTCTTAGG AAGAACTGGA TCAGG  25

( 2 ) INFORMATION FOR SEQ ID NO:50:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: synthetic oligonucleotide ( i i i ) SEQUENCE DESCRIPTION: SEQ ID NO: 50:

TTTCAGAGCA GTAATTTGCG TCCG  24

( 2 ) INFORMATION FOR SEQ ID NO:51:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: synthetic oligonucleotide ( i i i ) SEQUENCE DESCRIPTION: SEQ ID NO: 51:

ATCGGTGTTT CCTATGATGA GTAC  24

( 2 ) INFORMATION FOR SEQ ID NO:52:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: synthetic oligonucleotide ( i i i ) SEQUENCE DESCRIPTION: SEQ ID NO: 52:

ATAGGAAACA CCGATGATAT  20

( 2 ) INFORMATION FOR SEQ ID NO:53:

( i ) SEQUENCE CHARACTERISTICS:
    ( A ) LENGTH:18 base pairs
    ( B ) TYPE: nucleic acid -continued (C) STRANDEDNESS: single
(D) TOPOLOGY: linear (ii) MOLECULE TYPE: synthetic oligonucleotide (iii) SEQUENCE DESCRIPTION: SEQ ID NO: 53:

ATCATAGGAA ACACCGAT                                                          18

(2) INFORMATION FOR SEQ ID NO:54:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: synthetic oligonucleotide (iii) SEQUENCE DESCRIPTION: SEQ ID NO: 54:

ATAGGAAACA CCAAAGATGA                                                        20

(2) INFORMATION FOR SEQ ID NO:55:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: synthetic oligonucleotide (iii) SEQUENCE DESCRIPTION: SEQ ID NO: 55:

ATCATAGGAA ACACCAAA                                                          18

METHOD AND ASSAY FOR DETECTION OF THE EXPRESSION OF ALLELE-SPECIFIC MUTATIONS BY ALLELE-SPECIFIC IN SITU REVERSE TRANSCRIPTASE POLYMERASE CHAIN REACTION

This Application is based on the Provisional application Ser. No. 60/005,254 filed on Oct. 10, 1995, and is a continuation-in-part of the U.S. patent application Ser. No.: 08/487,799, filed on Jun. 7, 1995, pending, which is a continuation-in-part of the application Ser. No.: 08/409,544, filed on Mar. 24, 1995, abandoned, which is a continuation of the application Ser. No.: 07/933,471, filed on Aug. 21, 1992, abandoned.

BACKGROUND OF THE INVENTION

1. Field of Invention

This invention concerns a method and an assay for detection and differentiation between expression of unmutated wild-type DNA sequences and between endogenous DNA sequences in vitro or in vivo. Specifically, the invention concerns the method and the allele-specific in situ reverse transcriptase polymerase chain reaction (RT-PCR) amplification assay for detection and differentiation between expression of unmutated wild-type DNA sequences and between endogenous mutant DNA sequences or visa versa. The method is useful for verification, diagnostic assessment and monitoring of therapeutic small fragment homologous replacement gene therapy, for diagnostic assessment and monitoring of cDNA-based gene therapies, for analysis of gene expression of specific alleles during fetal development and for diagnostic assessment of the expression of alleles involved in cancer mutations.

2. Background Art and Related Disclosures

Gene therapy as a means of treating human genetic disease has been brought into the forefront in recent years by its application for the treatment of a variety of diseases including adenosine deaminase deficiency (ADA) as described in *Transplantation Proc.*, 23:170 (1991) and cystic fibrosis (CF) as described in *Nature Med.*, 1:39 (1995), *Nature Genet.*, 8:42 (1994), and *Cell*, 75:207 (1993).

Other human diseases which are potential targets for gene therapy include but are not limited to thalassaemias, sickle-cell anemia, xeroderma pigmentosum, Fanconi's anemia, ataxia telangiectasia, and muscular dystrophy.

There are many different approaches to the gene therapy that involve either introduction of therapeutic cDNA or genomic DNA replacement.

Recently, the U.S. Pat. No. 4,950,599 described a method for exchanging homologous DNA sequences in a cell using DNA fragments encapsulated in polyoma capsid, a protein coat of a virus particle. The frequency of homologous recombination in this system was very small, only about on the order of $10^{-5}$, and no means were described to determine to what extent the exogenous DNA fragments were able to induce reversion to hypoxanthine phosphorybosyl transferase (HPRT) positive phenotype without spontaneous homologous recombination.

Another distinct homologous replacement strategy recently developed methods for gene therapy that involve replacement of mutated sequences with wild-type "normal" nonmutated sequences. A new method for gene therapy was developed in attempts to correct mutated genes in situ by small fragment homologous replacement (SFHR) of mutated sequences in mammalian cells. This method provides a targeted gene replacement, using relatively small genomic DNA fragments with noncoding sequences flanking the sequences to be altered to replace endogenous sequences that are virtually homogenous.

In addition to cDNA-based gene therapy strategies, the SFHR method when applied in vivo is useful for gene therapy treating human genetic diseases and for countering the deleterious effects of these diseases. However, unlike the cDNA-based strategies, this method circumvents inappropriate cell expression and the physiological and metabolic complications that result. However, as with other methods, other than to follow the physiological function of the corrected gene, there is no effective method available to determine, with any accuracy, the cellular distribution of corrected sequence versus mutant sequence expression and/or to determine whether the gene therapy and/or protocol used for gene therapy was successful.

It would, therefore, be extremely useful to have available a method which would enable determination and differentiation of expression of endogenous mutated sequences and expression of the wild-type nonmutated sequences on a cell specific basis which method would enable both qualitative and quantitative assessment of gene therapy efficacy.

It is an object of the present invention to provide a method and an assay for detection of and differentiation between expression of endogenous DNA present in the cells from expression of exogenous wild-type DNA or DNA after gene therapy suitable for qualitative and quantitative assessment of efficacy of gene therapy.

All patents, patent applications, articles, references, standards and the like cited in this application are incorporated by reference in their entirety.

SUMMARY

One aspect of the current invention is a method for detection of expression and for differentiation between mRNA expression of endogenous mutated gene DNA sequences and mRNA expression of exogenous wild-type normal correcting DNA.

Another aspect of the current invention is a method for detection and differentiation of expression of endogenous mutated DNA and exogenous wild-type DNA using an assay comprising a reverse transcriptase polymerase chain reaction amplification of mRNA-derived DNA, cDNA or DNA fragment sequences.

Yet another aspect of the current invention is a method for detection and differentiation of expression of endogenous mutated DNA and exogenous wild-type DNA with an allele-specific detection of expressed gene using allele-specific primers.

Still another aspect of the current invention is a method for detection and differentiation of expression of endogenous mutated DNA and exogenous wild-type DNA using the first allele-specific primer for endogenous mutated DNA sequence, the second allele-specific primer for therapeutic nonmutated wild-type DNA sequence and the non-allele specific third primer specific for a DNA sequence in an exon that is outside of the region of homology defined by the wild-type therapeutic DNA.

Another aspect of the current invention is an allele-specific primer specific for an endogenous mutated or nonmutated gene.

Another aspect of the current invention is an allele-specific primer specific for a therapeutic nonmutated wild-type DNA fragment.

Another aspect of the current invention is an mRNA-specific primer for the reverse transcriptase reaction from DNA to cDNA.

Still another aspect of the current invention is a method useful for evaluation of gene therapy protocol, and for verification, management and determination of efficacy of gene therapy.

Still yet another aspect of the current invention is a method for diagnosis of genetic diseases during fetal development by detecting expression of the mutant allele in fetal cells.

Still another aspect of the current invention is a method for the diagnostic assessment of the expression of mutant alleles involved in cancer comprising detection of cancerous mutations present in precancerous cells having a normal phenotype.

Another aspect of the current invention is a diagnostic assay for detection of and differentiation between gene expression in tested tissue which is mutated or nonmutated, and gene expression in the same type normal tissue, which method comprises steps:

(a) obtaining a sample of the tested tissue cells;
(b) fixing the cells;
(c) digesting the cells of the sample of step (b) to expose the single strand mRNA and eliminate DNA contained in the cells;
(d) subjecting the mRNA of step (c) to reverse transcription reaction to obtain first-strand complementary DNA (cDNA) from the mRNA template of the sample of cells of step (a);
(e) subjecting the cDNA of step (d) to polymerase chain reaction amplification using allele-specific primers for tested tissue and a solution comprising all necessary nucleotides in sufficient quantity to obtain the cDNA in sufficient amount for the assay, wherein at least one nucleotide in the solution or in the primer is labelled with a non-interfering radioactive, immunochemical or fluorescent marker detectable by spectroscopic, autoradiographic emulsion, immunocytochemical or enzymatic detection means;
(f) obtaining a sample of the tissue cells of the same type of nonmutated tissue as in step (a) or tissue submitted to gene therapy or a sample of wild-type DNA fragment corresponding to nonmutated normal DNA;
(g) fixing the cells of step (f);
(h) digesting the cells of the step (g) to expose the single strand mRNA and eliminate DNA contained in the cells;
(i) subjecting the mRNA of step (h) to reverse transcriptase reaction to produce first-strand complementary DNA (cDNA) from the mRNA template of the cells of step (h);
(j) subjecting the cDNA produced in step (i) to polymerase chain reaction conditions using allele-specific primers for nonmutated tissue a solution comprising the necessary nucleotides, with the proviso that at least one nucleotide is labelled with a non-interfering radioactive, immunochemical or fluorescent marker which is detectable by spectroscopic means, immunoreaction means, autoradiographic means or by enzymatic detection means; and
(k) comparing the results obtained in step (e) with the results obtained in step (j) and observing the presence or absence of the detectable marker produced in step (j) in cDNA of step (e) to determine quantitatively or qualitively the presence of allele-specific mutation in the endogenous gene expression using spectroscopic, autoradiographic or enzymatic detection means.

Another aspect of the current invention concerns an assay method to verification, management and assessment of efficacy of gene therapy using differentiation between gene expression in tested mutated tissue which has been subjected to gene therapy and gene expression in the similar or the same type of normal tissue, which method comprises:

(a) obtaining a sample of the tested tissue cells subjected to gene therapy using small fragment homologous replacement of the endogenous DNA with the wild-type DNA with a sample of wild-type DNA fragment corresponding to the nonmutated normal DNA;
(b) fixing the cells of step (a);
(c) digesting the cells of step (b) to expose the single strand mRNA and eliminate DNA contained in the cells;
(d) subjecting the mRNA of step (c) to reverse transcription reaction to obtain first-strand complementary DNA (cDNA) from the mRNA template of the sample of cells of step (a);
(e) subjecting the cDNA of step (d) to polymerase chain reaction amplification in the presence of allele-specific primers for tested tissue using a solution comprising all necessary nucleotides in sufficient quantity to produce the cDNA in sufficient amount for the assay, wherein at least one nucleotide in the solution or in the primer is labelled with a non-interfering radioactive, immunochemical or fluorescent marker detectable by spectroscopic means, immunocytochemical means, autoradiographic emulsion or by enzymatic detection means;
(f) obtaining a sample of normal nonmutated tissue cells;
(g) fixing the cells of step (f);
(h) digesting the cells of the step (g) to expose the single strand mRNA and eliminate DNA contained in the cells;
(i) subjecting the mRNA of step (h) to reverse transcriptase reaction to produce first-strand complementary DNA (cDNA) from the mRNA template of the cells of step (h);
(j) subjecting the cDNA produced in step (i) to polymerase chain reaction conditions using allele-specific primers for nonmutated tissue and a solution comprising the necessary nucleotides, with the proviso that at least one nucleotide is labelled with a non-interfering radioactive, enzymatic, immunocytochemical or fluorescent marker which is detectable by spectroscopic means, immunochemical means, autoradiographic means or by enzymatic detection means; and
(k) comparing the results obtained in step (e) with the results obtained in step (j) and detecting in the sample of step (e) the presence or absence and a quantity of at least one labeled marker present in the DNA produced in step (j) to determine quantitatively or qualitatively the effectiveness of the gene replacement.

Still yet another aspect of the current invention is an assay useful for detection of the expression of mutant genes during fetal development or for verification of successful gene therapy using small fragment homologous replacement in correction of the mutated gene associated with cystic fibrosis, Fanconi's anemia, sickle cell anemia, retinitis pigmentosa, xeroderma pigmentosa, ataxia telangiectasia, Bloom's syndrome, retinoblastoma, Duchenne's muscular dystrophy, or Tay-Sachs disease.

BRIEF DESCRIPTION OF DRAWINGS

The file of this patent contains at least one drawing executed in color. Copies of this patent with color drawings will be provided by the Patent and Trademark Office upon request and payment of the necessary fee.

FIG. 3A shows primer pair CF8B/CF6 resulting in 411 bp fragment. FIG. 3B shows primer pair CF7B/CF6 resulting in 414 bp fragment.

FIG. 5 shows RT-PCR analysis of CFTR mRNA from HTE-11 cells transfected with uncoated or coated 488-nt fragments in a dendrimer-DNA complex.

FIG. 9A shows the result of in situ PCR of 16HBE14o⁻ cells following DNAse treatment and reverse transcription (+rt). Only this micrograph is positive for the presence of wtCFTR in mRNA. The other 3 micrographs are negative. FIG. 9B shows the result of in situ PCR of ΣCFTE29o- cells after reverse transcription.

FIG. 9C shows the result of in situ PCR of 16HBE14o- without reverse transcription.

FIG. 9D shows the result of in situ PCR of ΣCFTE29o- without reverse transcription.

FIGS. 11A–B is an allele-specific in situ RT-PCRs in human tissue. FIG. 11A shows wild-type CFTR mRNA detected in normal bronchial tissue. FIG. 11B shows wild-type CFTR mRNA detected in normal human colon tissue.

FIG. 12A, shows wild-type CFTR mRNA detected in normal bronchial epithelial cells using a wild-type specific oligonucleo-tide primer pair. FIG. 12B shows detection of mutated CFTR mRNA in cystic fibrosis bronchial epithelial cells. FIG. 12C shows a detection of mRNA in mixed population of mutated and nonmutated wild-type cells.

DEFINITIONS

Figure 1:
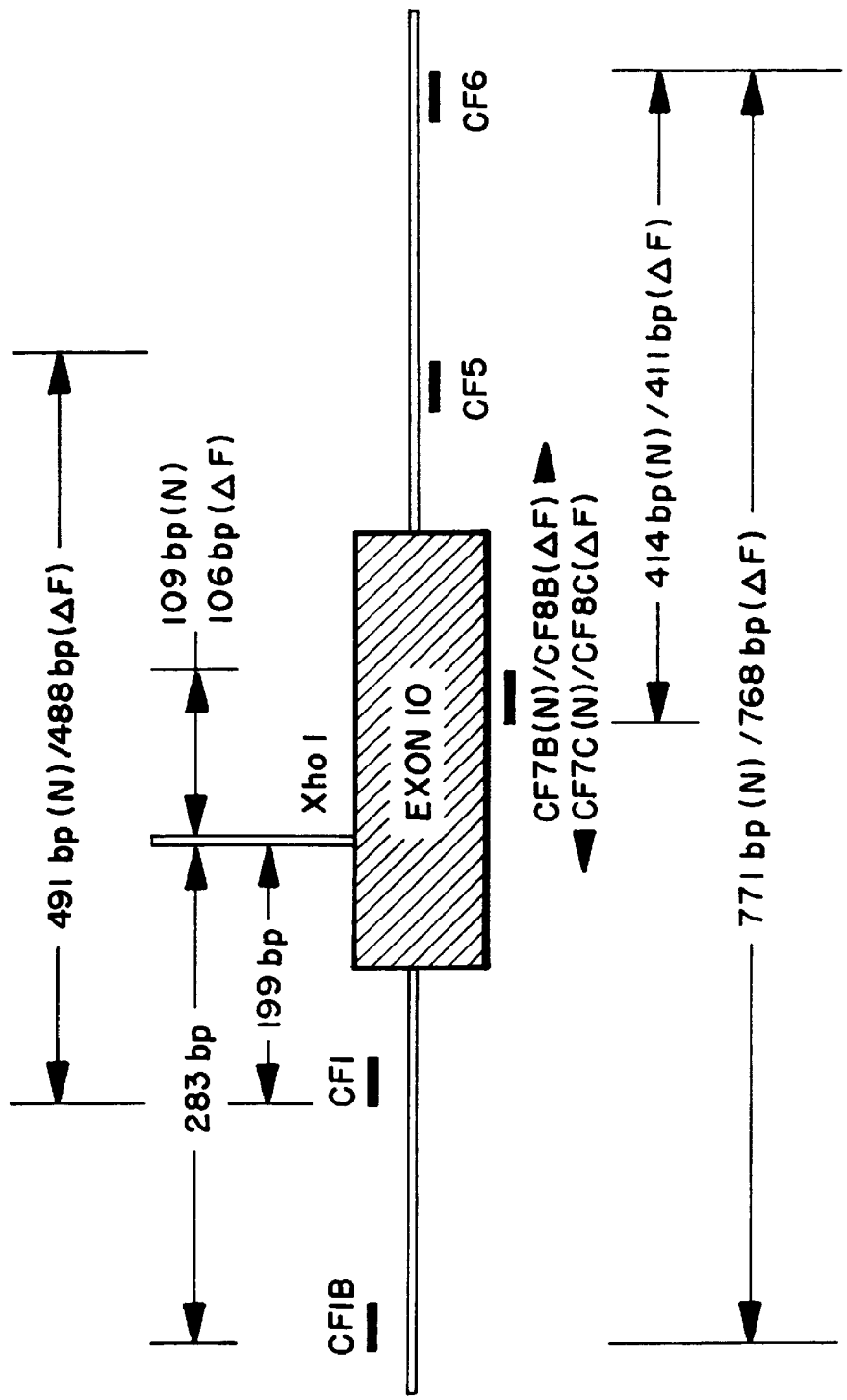
FIG. 1 is a schematic representation of the PCR analysis of genomic CFTR DNA amplifying the genomic locus containing the region targeted for SFHR of the ΔF508 mutation.

As used herein:

"Allele" means one of two or more alternate forms of a gene occupying the same locus on a particular chromosome. Alleles that functions normally are the wild-type alleles. Mutated alleles means alleles that function abnormally in comparison with the wild-type alleles.

"Wild-type or wt genomic DNA" means normal genomic DNA that does not contain a site that alters the amino acid sequence of the normal protein product and is not associated with a disease or dysfunction.

"Mutated DNA" means altered DNA sequence within a gene that results in a phenotype abnormality and causes and is manifested as a disease or dysfunction.

"Exogenous DNA" means the altering DNA used for changing endogenous genomic DNA sequences by small fragment homologous replacement. This DNA can be wild-type DNA used to correct a mutant gene or the mutant genomic DNA used to induce the mutation, for example, in transgenic animals serving as an animal model for study of the genetic disease, or the wild-type DNA serving as a standard for qualitative and quantative assessment of gene mutations or correction thereof by gene therapy. Exogenous DNA is used as a control "Endogenous DNA" means, for diagnostic purposes, a tested genomic DNA sequence present in the native gene, or for therapeutic purposes, the mutated DNA sequence to be altered by gene therapy. This DNA can either be cellular genomic DNA or pathogen genomic DNA. This DNA sequence is resident within a target cell for diagnosis or therapy.

"Gene therapy" means treatment of a patient suffering from a disease resulting from expression of genetic material that is mutated, i.e. its nucleotide sequence is different from the nucleotide sequence of a normal individual. Gene therapy thus means replacement of the dysfunctional gene with a functional gene.

"RT" or "reverse transcription" means mRNA directed DNA synthesis. The technique is described in *J. Biol. Chem.*, 260:9326 (1985), hereby incorporated by reference.

"PCR" or "polymerase chain reaction" means an enzymatic in vitro amplification of DNA sequences. The technique, described in *Science*, 239:1350 (1988) is hereby incorporated by reference.

"RT-PCR" means reverse transcriptase polymerase chain reaction. The reverse transcription polymerase chain reaction is according to the description of the art found in, for example, in U.S. Pat. Nos. 5,416,192; 5,416,260; 5,418,134; 5,418,149; 5,418,162; 5,420,009; 5,422,242; 5,424,184; 5,424,189; 5,426,026; 5,426,039; 5,427,909; 5,427,929; 5,427,932; 5,434,048; 5,435,309; 5,436,142; 5,436,144; 5,436,149; and 5,436,326, all of which are incorporated herein by reference.

DETAILED DESCRIPTION OF THE INVENTION

The current invention concerns a method and an assay which detects and differentiates between expression of therapeutic, normal nonmutated wild-type DNA and between mutated DNA in vitro or in vivo. The invention is useful for verification and assessment of gene therapy and in diagnostics.

Briefly, the assay involves allele-specific in situ reverse transcriptase polymerase chain reaction (RT-PCR) amplification of endogenous, typically mutated DNA and of exogenous, normal wild-type DNA or RNA. Expression of each of these DNAs and/or RNA is detected using labeled nucleotide marker or its precursor in the samples of the same cell types and results are qualitatively and quantatively compared to determine whether the mutated or normal DNA is completely, substantially or predominately expressed.

The method and the assay are useful for monitoring and verifying the success of a small fragment homologous replacement (SFHR) gene therapy of a specific region within genomic DNA. SFHR therapy comprises identifying certain typically mutated sequence within genomic DNA, obtaining and introducing (in vivo or in vitro) into cells that contain the mutated sequence a population of small endogenous or wild-type therapeutic DNA fragments that contain both exon and flanking noncoding sequences. These small fragments of exogenous DNA which are able to correct mutant genomic DNA sequences by homologous replacement, are expressed in the cells. The expressed exogenous DNA as mRNA and ultimately as protein leads presumably to correction of the dysfunction caused by the mutated gene. Until today, however, no method was available to verify and/or quantify the successful replacement of mutated DNA with therapeutic nonmutated DNA.

In this context, the invention is also useful for designing and testing the gene therapy protocol before the gene therapy is used, and for testing and designing allele-specific and allele-non-specific primers.

Additionally, the invention is useful for a variety of diagnostic assays for monitoring expression of disease genes in specific tissue. In this context, the invention is useful for detection of the expression of mutant alleles during fetal development or for detection of precancerous cells having a normal phenotype but carrying cancer mutations.

I. Assay for DNA Detection of Expression Using RT-PCR

The assay according to the invention is used for in situ detection of RNA expression for diagnostic and therapeutic purposes.

Generally, tissue is obtained from the tested individual typically suffering from the genetic disease or having family history or other predisposition to genetic disease, cancer, etc. For example, in case of cystic fibrosis, human bronchial or lung biopsies, or cells or cell lines from normal patients (wild-type DNA) and from cystic fibrosis patients (mutated DNA) are obtained or in case of, for example, skin melanoma, the healthy skin cells and suspect precancerous cells are obtained and used in this assay.

Site of the mutation is derived from the difference between the normal (wild type) sequence and the sequence obtained from the individual suffering from the disease controlled by that particular gene. For example, the most common mutation ΔF508 of the cystic fibrosis transmembrane conductance regulator (CFTR) is found in exon 10, and results in a phenylalanine deletion in the CFTR protein. The mutation causing sickle cell anemia is caused by an A to T transversion in the sixth codon of the human β-globin gene resulting in a glutamine to valine substitution in the protein. The mutation causing xeroderma pigmentosum group G is due to a deletion of an A in a run of AAA of the exon containing the mutation, as well as mutated sequences.

Next, a wild-type DNA sequence homologous to the site of the mutation but not containing the mutation is obtained. The wild-type sequence may be isolated or synthesized. The synthesis of the short homologous DNA fragment (wild-type DNA fragment) may be conducted by methods known in the art, such as the isolation and separation of a wild-type DNA fragment by cleavage with restriction endonuclease, PCR amplification, de novo oligonucleotide synthesis, and/or combinations of enzyme restriction and ligation to produce deletions, additions or the like.

Wild-type DNA fragments of the region where the DNA mutation occurs are isolated, for example, as described in Example 1 and the allele-specific primers are prepared to that particular region.

Allele-specific primers are prepared to the endogenous mutated DNA or RNA. Additionally, primers are prepared which are non-allele specific. These primers are specific for a DNA sequence in an exon other than the exon containing the mutation and are outside of the region of homology which is defined by the therapeutic or by the normal wild-type DNA fragment. Additionally, primers for the reverse transcriptase reaction from mRNA to DNA are prepared. These primers contain sequences complementary to the mRNA as well as sequences that are unique and not specific for any mRNA sequences. One non-allele specific PCR primer is based on the unique sequence found in the reverse transcription primer.

Conditions used for PCR amplification of individual primers are found in Example 2.

In the assay, briefly, cells obtained from the tested tissues are subjected to conditions under which the single strand mRNA is exposed. For the assay on the same slide, three drops of one of the samples are used. One drop is submitted to DNase and RT to detect mRNA. The second drop serving as a negative control is submitted to DNase but is not reverse transcribed. The third drop, which serves as a positive control is not submitted to DNase but is reverse transcribed.

Both positive and negative controls on the slide are used as methodology internal control and not for assessment of the expression of allele mutations. Typically, the cells are grown to about 70% confluence and are trypsinized, washed, for example, in phosphate buffer saline and resuspended in the same buffer, as cytospins on slides, such as SUPER-FROST PLUS slides, obtained from Fisher Company or Perkin Elmer. Cells are fixed in any suitable fixation solution, such as about 4% paraformaldehyde in IX PBS (PFA) and stored at about −80° C. until used. In the alternative, they are used without freezing. Cells fixed on slides are submitted to heating at about 35°–50° C., preferably 55° C. for about 10–30 minutes to bind the cells to the slides. Cells are then digested, and/or permeabilized for example, with trypsin pepsin 2 mg/ml in 0.1N HCl (0.01–0.05%), pronase (1–10 µg/ml) or other digestive enzyme, or chemical agents, such as 1.5 MNall, 0.1 MNaOH[1], 70% EtOH or 0.5% NP-40 for a time which is dependent on length of time of fixation, typically for about 5–45, preferably 10–30 minutes. During the digestion, the tissue or cells are permeabilized, mRNA is exposed and proteins, enzymes, etc., which could interfere with PCR are destroyed.

Slides are then dehydrated and treated with DNase (1 U/µl) for 4–29 hours, preferably overnight, at 20°–50° C., preferably at 37°–42° C., to remove genomic DNA which can interfere with the experiment and to obtain detectable single stranded mRNA. Cells are again washed and one of two sections or cell spots treated with DNase is submitted to reverse transcription, using methods known in the art.

Typically, the sample is treated in RT buffer, such as, for example, Perkin Elmer reverse transcriptase buffer, dithioerythriol (DTT), each nucleotide (0.5–1 mM), primers (1–3, in antisense primer or poly dt or random primers preferably 2 ul) RNasin (1–2.5 µl) and reverse transcriptase and 2500 µ/ml (about 1 µl). The solution is covered and placed in a humid chamber at 30°–50° C., preferably at 42° C., for about 10–120 minutes, preferably for 45 minutes, and reverse transcribed. The samples are then washed with PBS. Alternatively, all the above steps, such as fixation, digestion, permeabilization, reverse transcription and polymerase chain reaction can be performed using other agents and conditions as known now or will become known in the future as long as they in general can perform functions, as described.

To ensure the correct interpretation of the results, the proper controls must be included in the assay. All three sections or cell drop spots as described above, must be on the same slide. The tested section is treated with both DNase and is reverse transcribed (RT). The other two sections on the slide are the positive control (−DNase,+RT) and the negative control (+DNase,−RT). The positive control should show staining strongly in the nucleus, the negative control should show no staining. The tested sample should show, if positive, the marker present in the cytoplasm.

DNase digestion is necessary to remove genomic DNA which would interfere with detection of mRNA by RT-PCR because the genomic DNA can incorporate labeled nucleotide and would result in false positive or false negative results. DNase digestion achieved, for example, with 1 U/μl in 1M sodium acetate pH 5, 5 mM $MgSO_4$ is typically done overnight at 30°–50° C., preferably at 37° C. on two of the three sections, followed by a wash and dehydration step. The reverse transcription step is performed on one of the DNased sections and on the non-DNased section, typically in 50 ul per sample using Perkin Elmer solutions, containing 1× RT buffer, 1 mM DTT, 1 mM each dNTP, 1 μM antisense primer or poly dt, 2500 u/mL M-MLV, or Superscript II, BRL 2000 u/mL. Parafilm coverslips are added, samples are placed in a humid chamber at 42° C. for 45 minutes and washed.

The PCR reaction is done on all sections in 50 ul per section in a 50 μl final volume; 1× PCR buffer II, 200 μM each nucleotide, 10 μM each primer, 4.5 mM $MgCl_2$, 10 μM fluorescein labelled d-UTP (Boehringer mannheim), and 10 units of Taq (Is) DNA polymerase are added. A hotstart is performed with the Perkin Elmer in situ PCR system 1000 thermal cycler; 25 cycles, target temperature, 59° C. Slides are subsequently washed in 0.1×SSC, at 42°–55° C. for about 20 minutes to remove excess nucleotides. All methods and conditions involved in the assay, reverse transcriptase alone, PCR alone or both together could alternatively be performed or achieved with, for example, rTh DNA polymerase, obtained from Perkin Elmer, or using any other reverse transcriptase or DNA polymerase, at higher temperatures and under other suitable conditions. All these methods and conditions are intended to be within the scope of this invention.

This technique may be modified for various tissue materials by replacing fluorescein d-UTP with any of the following modified dNTPs: 10 μM digoxigenin or biotin-11-dUTP, or radioactively labelled d-UTP-either $^{33}P$ or $^{35}S$.

For qualitative and/or quantitative assessment, the amplified product is examined for the presence of the marker whether fluorescent, radioactive, chemical or immunochemical. Qualitative assessment simply detects the presence of the fluorescence or radioactivity in the cytoplasm for positive finding or absence of the marker for negative finding, depending on the allele-specific primers. For example, if the fetal diagnosis for cystic fibrosis is desired, the fetal bioptic tissue is treated as described and cystic fibrosis allele-specific primers are used. If the fluorescence or radioactivity is detected with these primers, then the tissue is positive for cystic fibrosis mutations. If, for example, the assay is used to determine successful gene therapy, the bioptic tissue of the treated individual is treated according to the invention, using wild-type allele-specific primers for detection of expression of normal nonmutated wild-type DNA. If gene therapy was successful, then there is fluorescence or radioactivity detected with these wild-type allele-specific primers. Quantitation of the expression in the cells is by counting the cells expressing the normal or mutated DNA or by using histograms or signal images, as described below.

Slides are viewed for fluorescence using any suitable fluorescent microscope, such as the Zeiss axiophot fluorescent microscope (450–490 nm wave length fluorescent epilumination) or a confocal microscope. Relative fluorescence per pixel of image may be compared using the confocal's histogram function. To determine fluorescent staining intensity of digitized grey scale images of cells or tissues captured in PHOTOSHOP from the Zeiss microscope the NIH image program may be used.

To detect the digoxigenin or biotin label, immunocytochemistry is carried out using standard protocols and anti-dig or anti-biotin antibody (Fab fragment, alkaline phosphatase conjugate. Briefly, slides are incubated in blocking buffer for 30 minutes at room temperature and washed in 0.1M Tris-HClpH7.9, 150 mM NaCl. About 50 ul of anti-dog or anti-biotin antibody diluted 1:200–1:500 in blocking buffer is applied to the sections. Slides are incubated at RT for 30 minutes to overnight in a humid chamber. Slides are then washed 2–3× in above wash buffer and then equilibrated for 2 minutes in 100 mM trisHCl at pH 9,5, 100 mM NaCl, 50 mM $MgCl_2$. Slides are then incubated in a NBT/BCIP substrate solution and developed for 5 minutes to 1 hour at room temperature. A purple precipitate will form. For in situ RT-PCR, color development will appear first over the cytoplasm, the cellular compartment where most mRNA is found.

To detect a radioactive label, autoradiography is carried out by dipping the slides in a photographic emulsion, such as Ilford K5D. Slides, stored in the dark at 4° C. are developed at various times (1 to 5 days) in Kodak developers and fixers. Autoradiographic grains are viewed in either dark or bright field using any suitable microscope such as the Zeiss axiophot microscope that detects fluorescence.

Obtained labeled DNA sequences are then compared for expression of mutated and/or wild-type DNA by following the presence or absence of the fluorescent, radioactive or chemical marker, as described above, for a qualitative assessment of gene therapy efficacy and quantitated by determining the number of cells expressing therapeutic RNA.

Confirmation of the allele specific RT-PCR technique is done by using conventional in situ hybridization techniques using preferably non-radioactive or radioactive DNA or RNA probes. After the PCR step, slides are washed and a labelled probe is applied in a hybridization solution for a number of hours. The hybridization buffer contains generally, 50% deionized formamide, 4×SSC, 10% dextran sulfate, 1× Denhardt's solution, 250 ug/ml tRNA. The slides are washed in stringent buffers, (0.1×SSC at 45°–55° C.) at the appropriate temperatures and the various detections systems (non-radioactive or radioactive) are used to detect the bound probe.

Confirmation of in situ product integrity is achieved by scraping the tissue off the slide after in situ PCR and extracting the DNA (TRIzol reagent, obtained for Gibco). The DNA is analyzed by agarose gel electrophoresis and Southern blot with the appropriate radioactive probe.

II. Detection of DNA Expression In Cystic Fibrosis

The assay and method of the invention were developed and tested on cystic fibrosis mutated and wild-type sequences. The method is, however, equally applicable to other sequences.

Accurate detection of cystic fibrosis transmembrane conductance regulator (CFTR) expression on a cell-by-cell basis has greatly facilitated understanding of its distribution in tissue. Not only does cell specific detection of CFTR help define the distribution, it is useful for assessment of gene therapy efficacy and for verification of gene therapy occurrence.

One problem in gene therapy, as described above, has been limitations in the direct detection of cells which are expressing the correcting genetic material. At the present time, there are no antibodies that differentiate wild-type (wt) CFTR from mutant CFTR. Even the most common CFTR mutation, the ΔF508, cannot be distinguished from wtCFTR protein immunocytochemically. The same is true for verification of other gene replacement.

The approach utilized in this invention is to evaluate expression of CFTR or expression of any other mutation at the level of mRNA. To distinguish wtCFTR from ΔF508 CFTR mRNA, the invention utilizes allele-specific reverse transcriptase polymerase chain reaction (RT-PCR) amplification in solution. This approach has not previously been directly applied to in situ analysis of cells in culture or in tissue sections.

To develop allele-specific in situ RT-PCR, a fluorescent nucleotide and allele-specific oligonucleotide primers are utilized to differentiate wtCFTR from mutated Δ508CFTR mRNA expression. By comparing a normal human bronchial epithelial cell line (16HBE14o-), to mutated ΔF508 homozygote airway epithelial cell lines (ΣCFTE29o- and CFBE4lo-), it is possible to distinguish between cells expressing wtCFTR and ΔF508CFTR. In addition, it is possible to distinguish the tissue sites of CFTR mRNA expression.

The importance of the method and assay of the invention for gene therapy is that it enables identification, both qualitative and quantitative, of the cells expressing the wild-type therapeutic DNA and distinguishes them from mutated cells expressing mutated DNA.

Typically, for SFTR the initial denaturation of the cells and cell tissue is conducted at 94°–5° C. for about 3 min. The second denaturation is performed at 94°–5° C. for about 1 min.

The annealing is performed at target temperature 59° C. for about 2 min. The initial elongation is performed at 72° C. for 1 min. The final cycle elongation is performed at 72° C. for 20 min. Usually 25 cycles of PCR are needed to obtain a useful amount of cDNA. The conditions, as described above, are modified for other cells or cells tissue, as needed. These modifications are within the skills of artisan.

A description of PCR and reverse transcription conditions are found in Examples 2, 5 and 6.

III. Target Genes for Therapy by Small Fragment Homologous Replacement

The present invention provides a method for verification, assessment of efficacy and monitoring of gene therapy performed to correct defects associated with genetic human diseases, such as cystic fibrosis, thalassaemias, sickle cell anemia, Fanconi's anemia, retinitis pigmentosa, Xeroderma pigmentosa, ataxia telangiectasia, Bloom's syndrome, retinoblastoma, Duchenne's muscular dystrophy, Tay-Sach's disease, and the like.

Genes and the mutation sites for diseases have been determined for a number of genetic disorders exemplified above. The mutant sequences and also the DNA sequences of the same, but normal gene alleles were used for preparation of allele-specific primers.

The gene that gives rise to cystic fibrosis, for example, encoding CF transmembrane conductance regulator (CFTR) contains more than 500 mutations that give rise to CF. The most common is a 3-bp, in frame deletion eliminating a phenylalanine at codon 508 (ΔF508). This deletion causes disturbance of chloride transport across epithelial membrane primarily resulting in diseases of gastrointestinal and respiratory systems. Typically, it causes chronic obstructive pulmonary disease, exocrine pancreatic insufficiency and abnormally high sweat electrolytes. Primers including allele-specific primers to the CF mutation are listed in Table 1. A sickle cell anemia β-globin gene is mutated at the sixth amino acid from the amino terminus of the β chain by replacement of glutamic acid with valine. The sickle cell hemoglobin contains the alteration in the β-globin primary structure which places an aberrant hydrophobic amino acid on the surface of the protein, causing deoxygenated hemoglobin to aggregate, resulting in alteration in the red blood cells shape and impedance of blood flow through capillaries and small venules. Primers including allele-specific primers are listed in Table 2.

Thalassaemias, the human genetic diseases, are caused by a failure to synthesize adequate amounts of hemoglobin α or β polypeptides. In several thalassaemias, mutations that create stop codons in the middle of the coding sequence prevent completion of the translation of mRNA, in others, mutations prevent normal intron splicing and therefore result in untranslatable mRNAs. Thalassaemias result in chronic microcytic anemias characterized by defective hemoglobin synthesis and ineffective erythropoiesis.

In xeroderma pigmentosum, complementation group G (XP-G), a 245 bp exon, contains a deletion of an adenosine (A) in a run of three adenosine (AAA) of bp 19–21 of the exon. This deletion leads to xeroderma pigmentosum, an inherited disorder in which afflicted individuals are hypersensitive to sunlight, in particular, ultraviolet (UV) light. Exposure to UV light results in skin cancer due to defective DNA repair. In the case of XP-G this defect is associated with an abnormal endonuclease. In addition, XP is often associated with central nervous system (CNS) defects. Primers including allele-specific primers for the XP-G complementation group are listed in Table 4.

There are numerous other genetic disorders and genes that lend themselves to the gene therapy protocols and therefore would be subject to verification by the method and assay of this invention. While the number of genes that could be altered by SFHR is large, a primary requirement is knowledge of the DNA sequence that constitutes a given gene. When this information is known or obtained, the invention provides a straight-forward method to design allele-specific primers that will be useful for detection of the expression of specific gene alleles. In addition to those diseases mentioned above, allele-specific in situ RT-PCR could be applied to adenosine deaminase deficiency (ADA), Lesch Nyhan syndrome, Duchenes muscular dystrophy, and Fanconi's anemia, to mention a few. Furthermore, the SFHR gene therapy protocol could be applied to the treatment of certain infectious diseases. All these diseases can be successfully diagnosed and their genetic abnormality can be characterized to be amenable to analysis by this assay.

IV. Detection and Diagnostic Utility

The assay of the invention is also useful for detection of mutations in fetal and other tissue as well as for early diagnosis of potential dysfunctions and disturbances caused by DNA mutations.

The assay, therefore, is used in detecting mutated genes in fetal tissue, for ammioanalysis and other tests typically used for early detection of the genetic disease.

For this purpose, the sample of the fetal tissue or amniotic fluid is obtained, mRNA of the suspected gene is obtained as described above and the presence or absence of the mutated DNA is determined by comparison with the wt DNA. If the normal wt DNA is expressed than the genetic disease is not present. If the normal wt DNA is not expressed or when the mutated DNA is expressed then the genetic disease is or will be present or there is a danger that it might develop.

Similarly, the suspect tissue of precancerous cell or cells from the predisposed patients, such as when there is a breast cancer family history, is submitted to the assay of the invention and the cancer mutation is either confirmed or not found. Early detection of precancerous cells provides an opportunity for early detection.

V. Allele-Specific Primers Used in the Assay of the Invention For Detection of Allele-Mutations The primer pairs used for PCR analysis were designed to be specific for the genomic locus in the regions where the mutation occurs.

Figure 2:
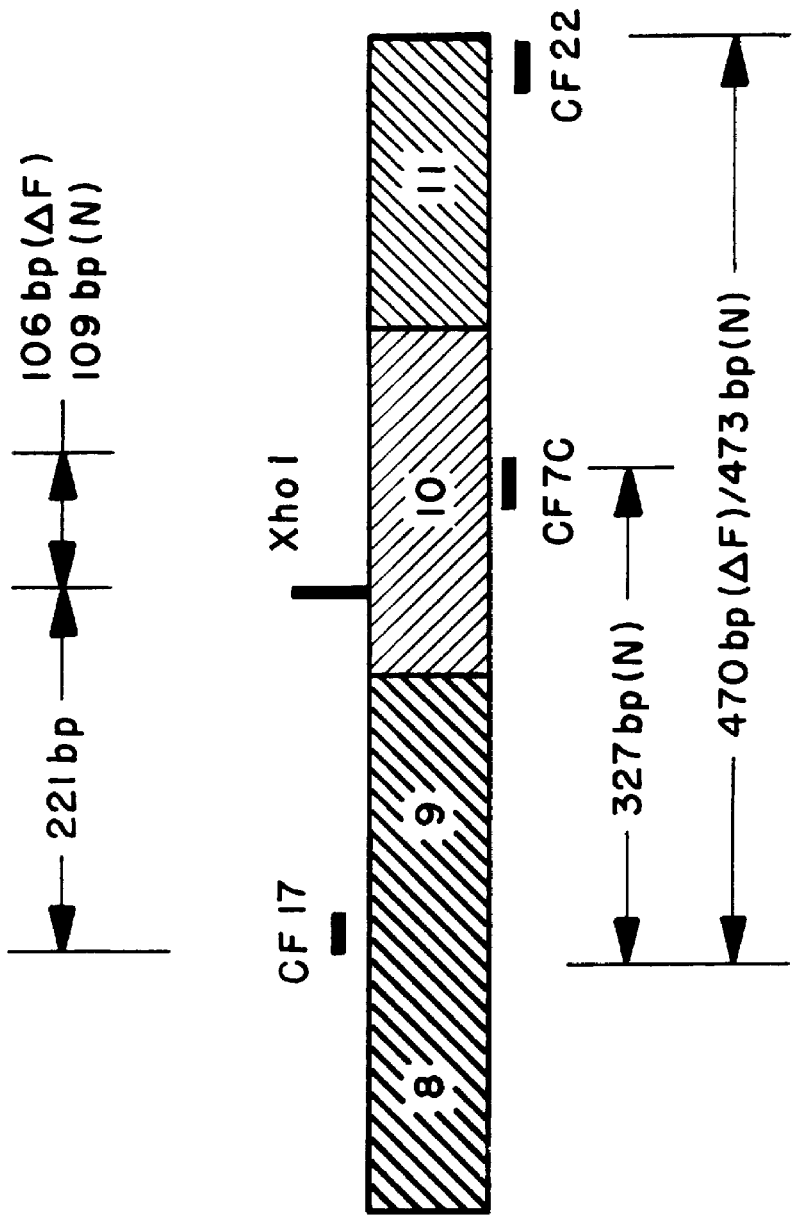
FIG. 2 represents a strategy for RT-PCR analysis of CFTR mRNA.

Cystic fibrosis primers are specific for genomic locus in the region of exon 10 that contains the homologous region. Primers indicated in FIGS. 1 and 2 are defined in Tables 1 and 2.

TABLE 1

Sequences of Primers and Oligonucleotides

| CF 1 | (S) 5'-GCAGAGTACCTGAAACAGGA-3' | SEQ ID NO: 1 |
|---|---|---|
| CF1B | (S) 5'-CCTTCTCTGTGAACCTCTATCA-3' | SEQ ID NO: 2 |
| CF5 | (A) 5'-CATTCACAGTAGCTTACCCA-3' | SEQ ID NO: 3 |
| CF6 | (A) 5'-CCACATATCACTATATGCATGC-3' | SEQ ID NO: 4 |
| CF7B | (S) 5'-CCATTAAAGAAAATATCATTGG-3' | SEQ ID NO: 5 |
| CF8B | (S) 5'-CCATTAAAGAAAATATCATTGG-3' | SEQ ID NO: 6 |
| CF7C | (A) 5'-ATAGGAAACACCAAAGATGA-3' | SEQ ID NO: 7 |
| CFBC | (A) 5'-ATAGGAAACACCAATGATAT-3' | SEQ ID NO: 8 |
| CF9 | (S) 5'-ACTTTAAAGCTGTCAAGCCGTG-3' | SEQ ID NO: 9 |
| CF14 | (A) 5'-CTGTATTTTGTTTATTGCTCCAA-3' | SEQ ID NO: 10 |
| CF 17 | (S) 5'-GAGGGATTTGGGGAATTATTTG-3' | SEQ ID NO: 11 |
| CF 22 | (A) 5'-CTTGCTAAAGAAATTCTTGCTC-3' | SEQ ID NO: 12 |
| oligo N | (A) 5'-CACCAAAGATGATATTTTC-3' | SEQ ID NO: 13 |
| oligo ΔF | (A) 5'-AACACCAATGATATTTTCTT-3' | SEQ ID NO: 14 |
| C16B | (B) 5'-CTTTTCCTGGATTATGCCTGGCAC-3' | SEQ ID NO: 15 |

TABLE 2

Primer sequences

| CF 1 | 5'-GCAGAGTACCTGAAACAGGA-3' | SEQ. ID NO: 1 |
|---|---|---|
| CF 1A | 5'-GCAGAGTACCTGAAACAGGAAGTA-3' | SEQ. ID NO: 32 |
| CF 1B | 5'-CCTTCTCTGTGAACCTCTATCA-3' | SEQ. ID NO: 2 |
| CF 1C | 5'-CTTGTCACACTGTATTGTAATTG-3' | SEQ. ID |

TABLE 2-continued

Primer sequences

| | | NO: 33 |
|---|---|---|
| CF 5 | 5'-CATTCACAGTAGCTTACCCA-3' | SEQ. ID NO: 3 |
| | 3'-GTAAGTGTCATCGAATGGGT-5' | SEQ. ID NO: 34 |
| CF 5A | 5'-CATTCACAGTAGCTTACCCATAGA-3' | SEQ. ID NO: 35 |
| | 3'-GTAAGTGTCATCGAATGGGTATCT-5' | SEQ. ID NO: 36 |
| CF 6 | 5'-CCACATATCACTATATGCATGC-3' | SEQ. ID NO: 4 |
| | 3'-GGTGTATAGTGATATACGTACG-5' | SEQ. ID NO: 37 |
| CF 7 | 5'-AGAAAATATCATCTTTGG-3' | SEQ. ID NO: 38 |
| CF 7B | 5'-CCATTAAAGAAAATATCATCTT-3' | SEQ. ID NO: 5 |
| CF 7C | 5'-ATAGGAAACACCAAAGATGA-3' | SEQ. ID NO: 7 |
| | 3'-TATCCTTTGTGGTTTCTACT-5' | SEQ. ID NO: 39 |
| CF 8 | 5'-AGAAAATATCATTGGTGT-3' | SEQ. ID NO: 40 |
| CF 8B | 5'-CCATTAAAGAAAATATCATTGG-3' | SEQ. ID NO: 6 |
| CF 8C | 5'-ATAGGAAACACCAATGATAT-3' | SEQ. ID NO: 41 |
| | 3'-TATCCTTTGTGGTTACTATA-5' | SEQ. ID NO: 42 |
| CF 16B | 5'-GTTTTCCTGGATTATGCCTGGCAC-3' | SEQ. ID NO: 43 |
| CF 16D | 5'-GTTGGCATGCTTTGATGACGCTTC-3' | SEQ. ID NO: 44 |
| | 3'-CAACCGTACGAAACTACTGCGAAG-5' | SEQ. ID NO: 45 |
| CF 17 | 5'-GAGGGATTTGGGGAATTATTTG-3' | SEQ. ID NO: 11 |
| CF 22 | 5'-CTTGCTAAAGAAATTCTTGCTC-3' | SEQ. ID NO: 12 |
| | 3'-GAACGATTTCTTTAAGAACGAG-5' | SEQ. ID NO: 46 |

The nucleotide sequence of CFTR DNA primers as described above were derived from published data. Sense (S) and antisense (A) primers are as indicated. The sense DNA strand codes for mRNA.

Classical sickle cell (SC) anemia is a disease caused by an A to T transversion in the sixth codon of the human beta-globin gene resulting in a Glu to Val substitution in the protein. Phenotypically there is a polymerization of the hemoglobin that results in a myriad of pathologies which ultimately lead to the death of the individual. The disease is subject to gene therapy and the success of the gene therapy is determined by the assay of the invention.

Primers used for analysis of homologous exchange and allele-specific expression are shown in Table 3.

TABLE 3

Sickle Cell Primers

| PRIMER | SEQUENCE | |
|---|---|---|
| SC1 (+) | 5'-TAGCAATTTGTACTGATGGTATG-3' | SEQ ID NO. 16 |
| SC2 (−) | 5'-TATACACAATTTAAGGCATTAG-3" | SEQ ID NO. 17 |
| SC3 (+) | 5'-CCCTGTGGAGCCACACCCTAGGGT-3' | SEQ ID NO. 18 |
| SC4 (−) | 5'-AACGATCCTGAGACTTCCACACT-3' | SEQ ID NO. 19 |
| SC5 (+) | 5'-ACATTTGCTTCTGACACAACTGTG-3' | SEQ ID |

TABLE 3-continued

Sickle Cell Primers

| PRIMER | SEQUENCE | |
|---|---|---|
| SC6 (−) | 5'-AGGGTTGCCCATAACAGCATCAG-3' | SEQ ID NO. 20 |
| SC-BA (−) | 5'-CTTCTCCTCAGGAGT-3' | SEQ ID NO. 21 |
| | | SEQ ID NO. 22 |
| SC-BS (−) | 5'-CTTCTCCACAGGAGT-3' | SEQ ID NO. 23 |

Primers SC5 and SC6 are used to assay mRNA expression of the DNA that has undergone homologous replacement.

Primers SC-BA and SC-BS are allele-specific and differentiate between wild-type (SC-BA) and sickle (SC-BS) β-globin sequences. The (+) and (−) designate sense and antisense sequences, respectively.

Another disease which can be treated by homologous recombination using small fragments in xeroderma pigmentosum, a disease of skin. Xeroderma pigmentosum is a rare, disfiguring syndrome inherited as an autosomal recessive trait.

Allele-specific analysis of the wild-type (N) sequences of the XP group G gene is detected by amplification with either primers XP3/XP6A (237-bp) and XP7A/XP4 (374-bp). The XP G mutation (AAA>AA) was assayed by amplification with primers XP3/XP6B (237-bp) and XP7B/XP4 (374-bp). Sense=(+), antisense=(−).

Allele-specific primers XP6A and XP7A detect normal (N) sequences and XP6B and XP7B detect the XP-G mutation. XP6A and XP6B are used in conjunction with XP3 to generate a fragment of 237-bp, while XP7A and XP7B are used with XP4 to give a product of 374-bp. Because the 374-bp fragment contains a Kpn I cut site, cleavage results in 97-bp and 277-bp restriction fragments. Non-allele-specific primers for XP-G exon sequences will be determined from published information.

For studies performed in vivo in mice, specific mouse murine SFTR cDNA primers were prepared. These primers are shown in Table 5.

TABLE 5

Murine CFTR cDNA Primers

| mCF11R | CTTGTGGGAAATCCTGTGCTGAA | SEQ. ID NO: 47 (exon 11) w/mCF508-3 |
|---|---|---|
| mCF12R | CCTTCTCCAAGAACTGTGTTGTC | SEQ. ID NO: 48 exon 11 |
| mCF20R | GGCTCTTAGGAAGAACTGGATCAGG | SEQ. ID NO: 49 exon 20 |
| mCF24R | TTTCAGAGCAGTAATTTGCGTCCG | SEQ. ID NO: 50 exon 24 |
| mCF508(−) | ATCGGTGTTTCCTATGATGAGTAC | SEQ. ID NO: 51 exon 10 |
| mCF508-2(−) | ATAGGAAACACCGATGATAT | SEQ. ID NO: 52 exon 10 |
| mCF508-3(−) | ATCATAGGAAACACCGAT | SEQ. ID NO: 53 exon 10 |
| mCFN-2(−) | ATAGGAAACACCAAAGATGA | SEQ. ID NO: 54 exon 10 |
| mCFN-3(−) | ATCATAGGAAACACCAAA | SEQ. ID NO: 55 exon 10 |

Table 4 lists DNA sequences primers used for generation of short homologous fragments in the region of a 245 bp exon of complementation group G.

RNA primers and specific conditions for PCR are seen in Table 6.

TABLE 4

Xeroderma Pigmentosum (XP) Group G PCR Primers

| PRIMERS | SEQUENCE | |
|---|---|---|
| XP1(+) | 5'-AGCATTTTTCAGGTTCCTCCAG-3' | SEQ ID NO. 24 |
| XP2(−) | 5'-AACCTACTTAACCTGGCTTCCT-3' | SEQ ID NO. 25 |
| XP3(+) | 5'-GGCTTGTTTTGAAGTTACAGGC-3' | SEQ ID NO. 26 |
| XP4(−) | 5'-AAGCCATCAGCAACCACAAGA-3' | SEQ ID NO. 27 |
| Allele-Specific primers | | |
| XP6AS(−) (N) | 5'-CCTCATCACTAATCACACTTTG-3' | SEQ ID NO. 28 |
| XP6B(−) (XP) | 5'-TCCTCATCACTAATCACACTTG-3' | SEQ ID NO. 29 |
| XP7A(+) (N) | 5'-GAAGTTTCATTGAAGTGCAAAG-3' | SEQ ID NO. 30 |
| XP7B(+) (ZXP) | 5'-GGAAGTTTCATTGAAGTGCAAG-3' | SEQ ID NO. 31 |

TABLE 6

PCR and Xho I Fragments

| PRIMERS | FRAGMENT SIZE DNA | PRIMERS | FRAGMENT SIZE RNA |
|---|---|---|---|
| CF1/CF5[a] | 491-bp(N) | CF17/CF7C[d] xHO 1 | 330-BP(n) 221-BP/109-BP |
| CF1B/CF6[b] | 771-bp(N) 768-bp(ΔF) | CF17/CF8C[d] Xho 1 | 327-bp(ΔF) 221-bp/106-bp |
| CF1B/CF7[b] Xho1 | 392-bp(N) 283-bp 109-bp | CF22/CF7B | 178-bp |
| CF1B/CF7C[b] Xho 1 | 389-bp(ΔF) 283-bp/106-bp | CF22/CF8B | 175-bp |
| CF1/CF7C[c] Xho 1 | 308-bp(N) 199-bp/109-bp | | |
| CF1/CF8C[c] Xho 1 | 305-bp(ΔF) 199-bp/106-bp | | |

FIG. 1 is a schematic representation of the PCR analysis of genomic DNA.

Primers CF1B and CF6 (Table 1) are outside the region of homology and amplify only DNA derived from genomic DNA around the region of homology.

Primers CF7B and CF8B are sense (+) allele specific primers for wt and ΔF508 CFTR sequences, respectively. In combination with CF6 (−) these primers give rise to a fragment that is either 414 bp or 411 bp that represent the presence of wt or ΔF508 CFTR sequences, respectively. Their usefulness as allele-specific primers is exemplified in FIGS. 3 and 4.

The CF7C and CF8C primers are antisense (−) and are allele-specific for wt and ΔF508 CFTR sequences, respectively. In conjunction with the sense (+) primer CF1B, they amplify fragments that are 391 bp or 389 bp wt- or ΔF508-specific, respectively. The restriction analysis with Xho I of the CF1B/CF7C or CF8C amplification product gives rise to two different restriction fragments of 283 bp and 109 bp (N) or 106 bp (ΔF). Their usefulness as allele-specific primers is exemplified in FIG. 7. If a secondary amplification is carried out with primers CF1/CF7C or CF8C, then the restriction fragments will be 199 bp and 109 bp (N) or 106 bp (ΔF).

FIG. 2 is a schematic representation of the PCR analysis of genomic DNA illustrating strategy for RT-PCR analysis of CFTR mRNA by spanning intron/exon boundaries. The resultant mixture of 473 bp (N) or 470 bp (ΔF) fragments was then purified and reamplified by allele-specific PCR with primers CF17/CF7C OR CF17/CF8C. Their usefulness as allele-specific RT-PCR primer pair are exemplified in FIGS. 3 and 4. The resultant 330 bp (N) or 327 bp (ΔF) fragments were digested with Xho I to determine if the genomic locus which has undergone homologous replacement is transcribed. The restriction fragments were either 221 bp and 109 bp (nonCF) and 221 bp and 106 bp (ΔF508).

Figure 3A:
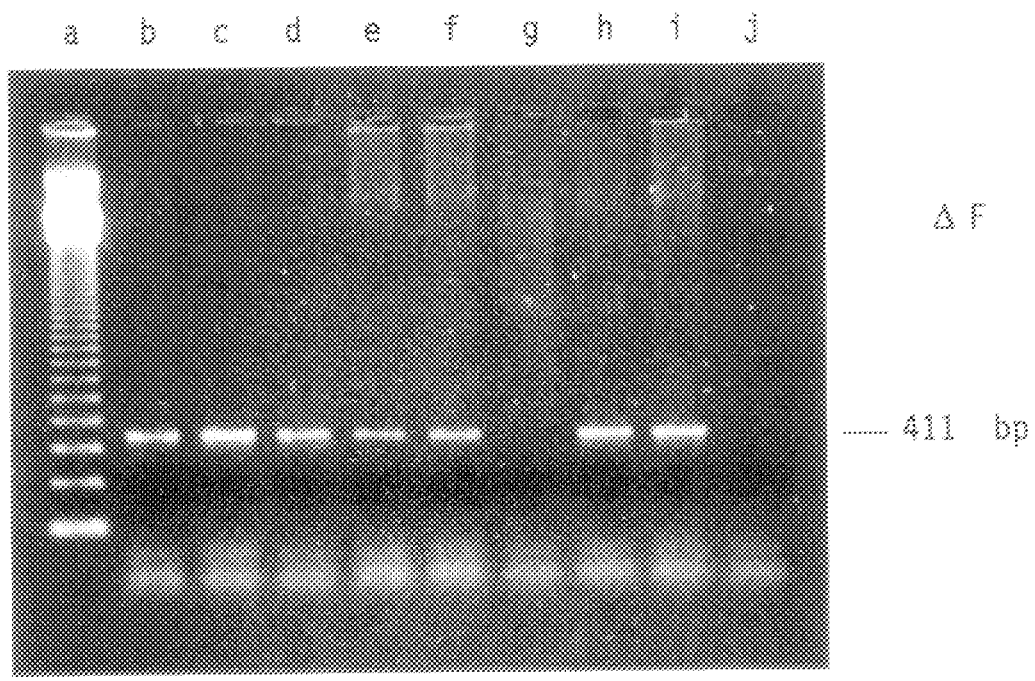
FIGS. 3A–B are allele-specific PCR analyses of transfected ΣCFTE29o- cells using primers CF7B/CF6(N) or CF8B/CF6(ΔF).
Figure 3B:
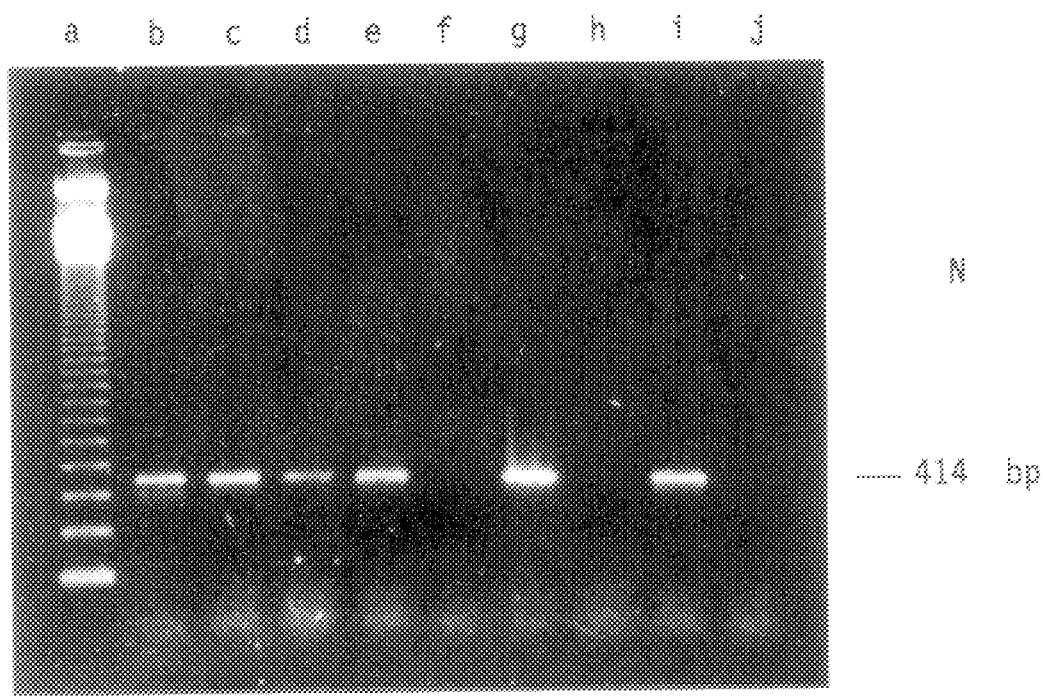

FIG. 3 shows allele-specific PCR analysis (using primers CF7B/CF7 (N) or CF8B/CF7 (ΔF)). FIG. 3 is an analysis of ΣCFTE29o- cells transfected either with the Starburst™ dendrimer-DNA complex (lanes b and c) or the gramicidin S-DNA-lipid complex (lanes d and e). DNA was either uncoated (lanes b and d) or coated with rec A (lanes c and e). In FIG. 3A, isolated DNA was amplified using primers CF8B/CF6 (top) and in FIG. 3B using primers CF7B/CF6 (bottom). Control samples were of DNA from ΣCFTE/con (lane f); nonCF (N/N) lymphocytes (lane g); ΔF508 homozygote (Δ/ΔF) lymphocytes (lane h); ΔF508 heterozygote (Δ/N) lymphocytes (lane i); and water (lane j). Wild-type CFTR sequences were only detected in the samples from transfected cells, and in the N/N and ΔF/N lymphocyte DNA samples.

Figure 4A:
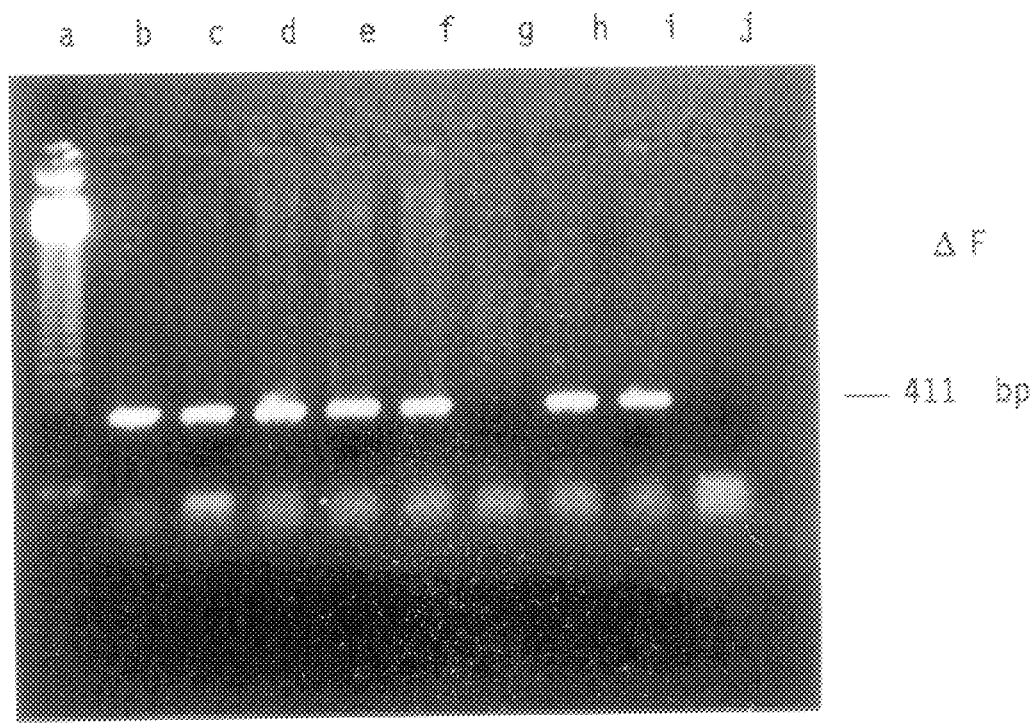
FIGS. 4A–4B are allele specific PCR analyses of CFPAC-1 cells with primers CF1A/CF7C transfected with rec A coated and uncoated 491 base fragments.
Figure 4B:
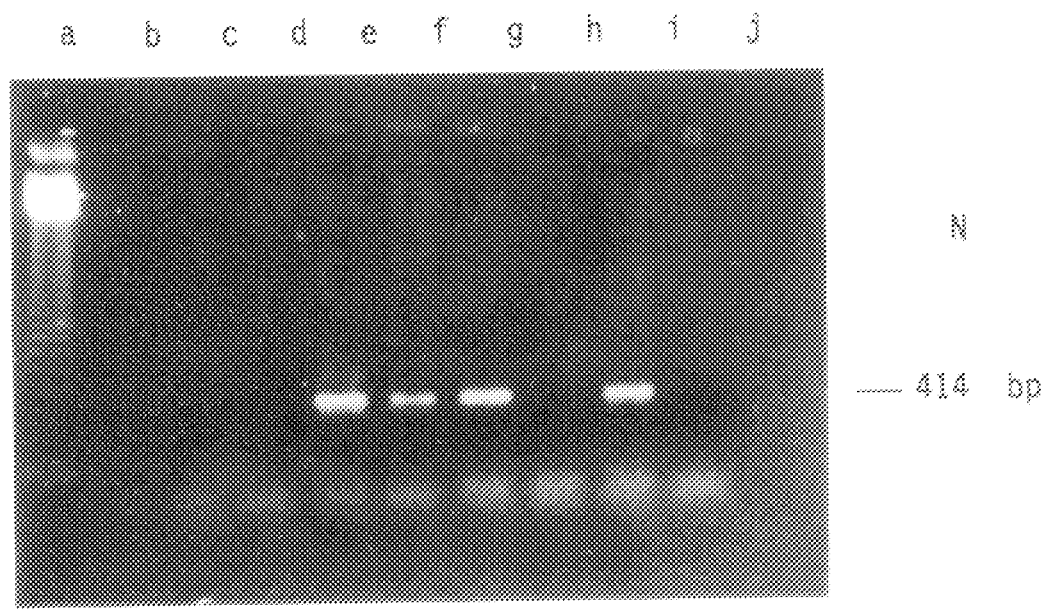

FIG. 4 shows allele-specific PCR analysis of CFPAC-1 cells transfected with rec A coated and uncoated 491 base fragments using the Starburst™ dendrimer-DNA complex to introduce the homologous DNA into the cells. PCR analysis of CFPAC-1 DNA from control nontransfected (lane b) and mock-transfected without DNA (lanes c and d). Cells transfected with fragment 9 (lanes e and f) and control DNA from the N/N and N/ΔF508 lymphocytes (lanes g and i) indicated the presence of wtCFTR sequences. Analysis for ΔF508 sequences indicated their presence in all samples except the control N/N lymphocyte DNA (lane g). No wtCFTR sequences were indicated in control nontransfected and mock-transfected (lanes b, c, and d) or the Δ/Δ lymphocyte (lane h) DNA. A 123-bp marker was used (lane a) and water controls were in lane (j) in all cases. Primers were as in FIG. 3.

FIG. 5 shows RT-PCR analysis of CFTR mRNA from HTE-11 cells transfected with uncoated (−) or rec A-coated (+) 488-nt fragments in a dendrimer-DNA complex. The cDNA was amplified with primer CF17 (exon 9) and primers specific for normal (CF7C, 330-bp fragment) or mutant (CF8C, 327-bp fragment) sequences. Digestion with Xho I only showed the expected 221-bp and 106-bp restriction fragments for DNA amplified with CF17/CF8C. Nontransfected controls are in the C lanes. The marker (123-bp) is in lane M.

Figure 6:
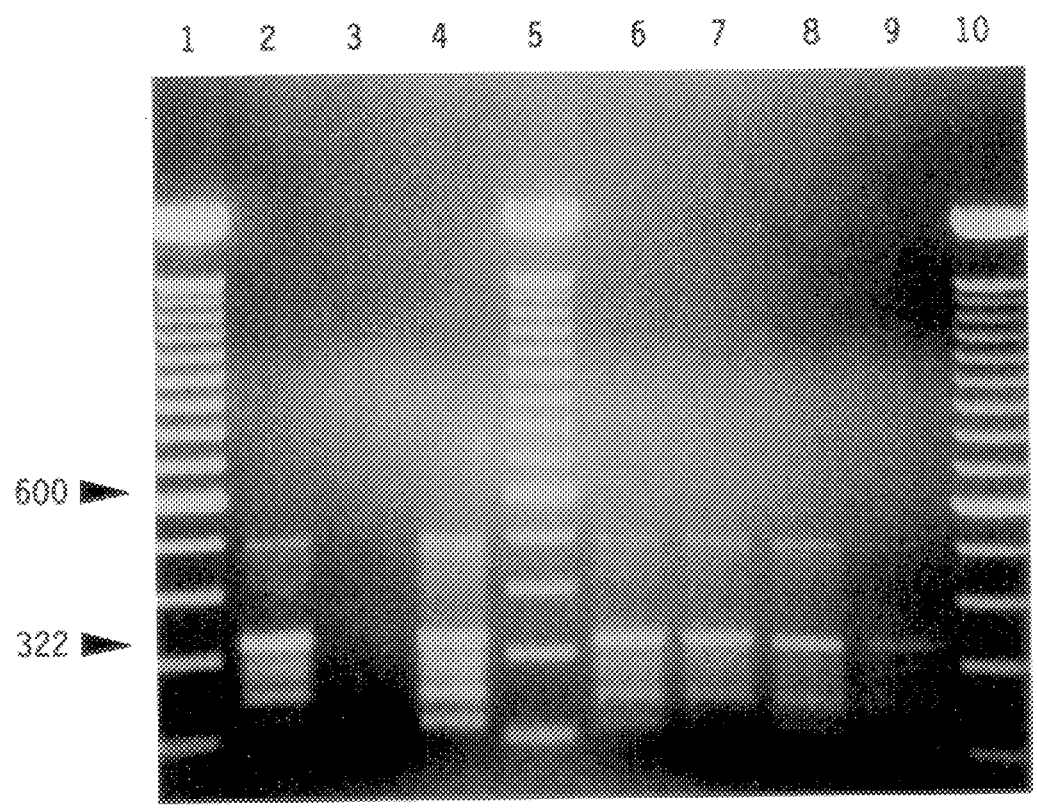
FIG. 6 is an autoradiographic analysis of DNA amplified from first-strand CFTR cDNA from ΣCFTE29o- cells.

Use of the assay of the invention for verification of gene therapy by following expression of corrected gene as mRNA is seen in FIG. 6.

FIG. 6 shows analysis of DNA amplified from first-strand CFTR cDNA from ΣCFTE29o- cells electroporated with rec A-coated 491-nucleotide fragments (lanes 6 and 7) or with rec A-coated or DNA fragments not coated with rec A, encapsulated as a gramicidin S-DNA-lipid complex (lanes 8 and 9), respectively. Cells were electroporated or transfected with the rec A-coated or uncoated 491 nucleotide fragments, and cytoplasmic RNA was isolated 7 days later. CFTR mRNA was reverse-transcribed into first-strand CFTR cDNA. The cDNA was amplified with CF17 (exon 9) primer and allele-specific primers for either normal (oligo N, 322-bp fragment) or mutant (ΔF,321-bp fragment) sequences. A 321-bp PCR fragment was produced in DNA from transfected ΣCFTE29o- cells when first-strand cDNA was amplified directly with the CF17/ΔF primer pair in control cells (lane 4). However, only control normal 16HBE14o- cells (lane 2) and electroporated and transfected cells (lanes 6–9) amplified with CF17/N produced a 322-bp band. No DNA product was observed when cDNA from ΣCFTE/con cells was amplified with the CF17/N primers (lane 3). Marker DNA (100-bp) is located in lanes 1, 5, and 10.

Results seen in FIG. 6 shows that corrected CFTR DNA has been expressed as mRNA and normal CFTR function has been restored. As seen in FIG. 6, allele-specific RT-PCR amplification of mRNA indicates that wtCFTR correcting DNA was transcribed in transfected cells. Amplification of genomic DNA was circumvented because the primers require amplification across intron/exon boundaries. These results indicate the usefulness of oligoN and oligoΔF as allele-specific primers.

Amplified cDNA from normal 16HBE14o- cells (lane 2) and experimentally transfected CF cells (lanes 6–9) yielded DNA fragments with the CF17/oligo N (322-bp). Amplified cDNA from ΣCFTE/con cells only showed a DNA fragment after amplification with the CF17/oligo ΔF (321-bp) (lane 4) but not with the CF17/oligo N primers (lane 3). Two separate electroporation experiments with the 491 nucleotide wtCFTR ssDNA fragments (lanes 6 and 7) showed the presence of wtCFTR mRNA. In addition, RNA from gramicidin S-DNA-lipid-transfected ΣCFTE29o- cells also contained wtCFTR mRNA whether or not the 491 nucleotide fragments were coated with rec A (lanes 8 and 9).

Figure 7:
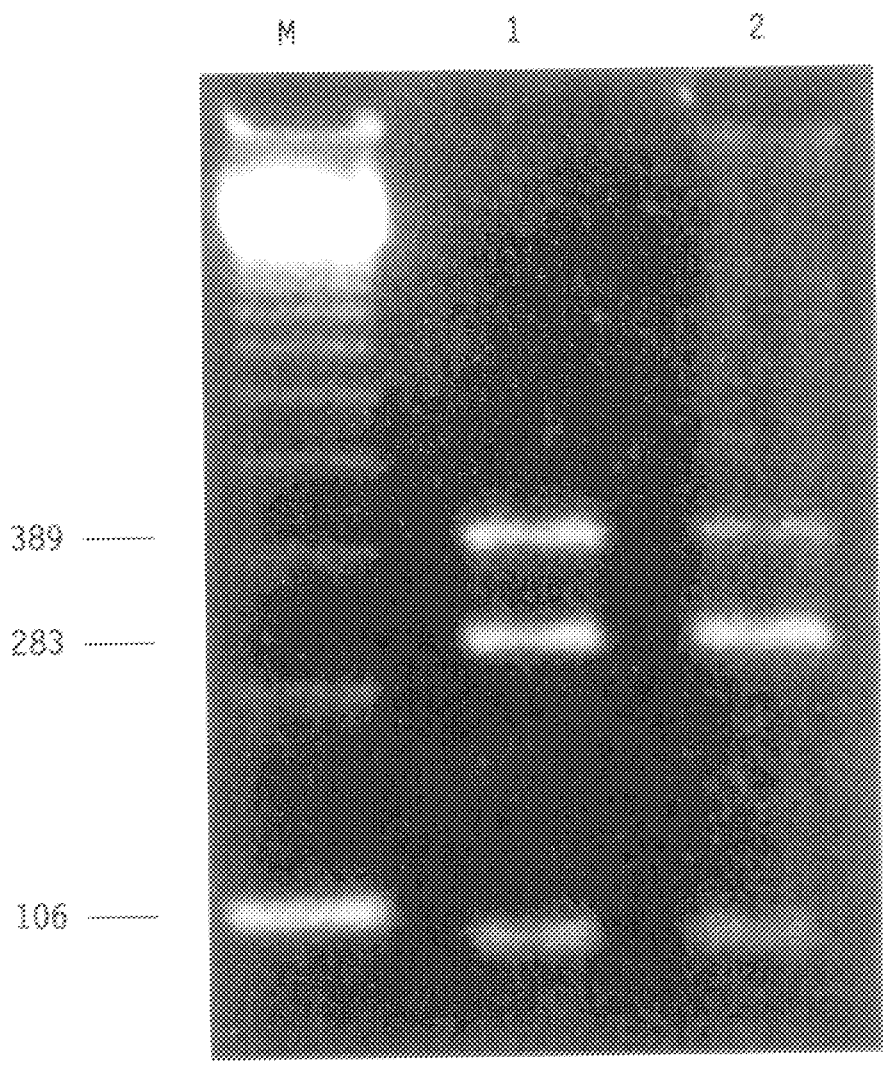
FIG. 7 illustrates restriction enzyme digestion analysis of the allele-specific amplification product generated with primers CF1B/CF8C from PCR amplification of DNA from nontransformed primary airway epithelial cells transfected with 488 base fragments containing the ΔF508 mutation and a unique XhoI restriction site.

FIG. 7 is restriction enzyme digestion analysis of the allele-specific amplification product generated with primers CF1β/CF8C. Primary nonCF airway epithelial cells were transfected with 488 base ssDNA fragments containing the ΔF508 mutation and an Xho I restriction enzyme site. PCR amplification of the DNA by primers CF–1B/CF7C gave a product of 389 bp. When the amplification product was cut by Xho I, fragments of 283 and 106 bp were detected (lanes 1 and 2). DNA was isolated from cells transfected with rec A-coated (lane 1) and uncoated (lane 2) 488 base fragments.

FIG. 7 shows that using PCR analysis of the DNA from nonCF primary airway epithelial cells that the cells have undergone homologous replacement with a 488 nucleotide ΔF508 DNA fragment. Restriction enzyme analysis of the PCR product generated from the genomic exon 10 locus further shows that the exogenous fragment replaced the endogenous sequences and in this way confirmed that the gene therapy was successful.

Figure 8:
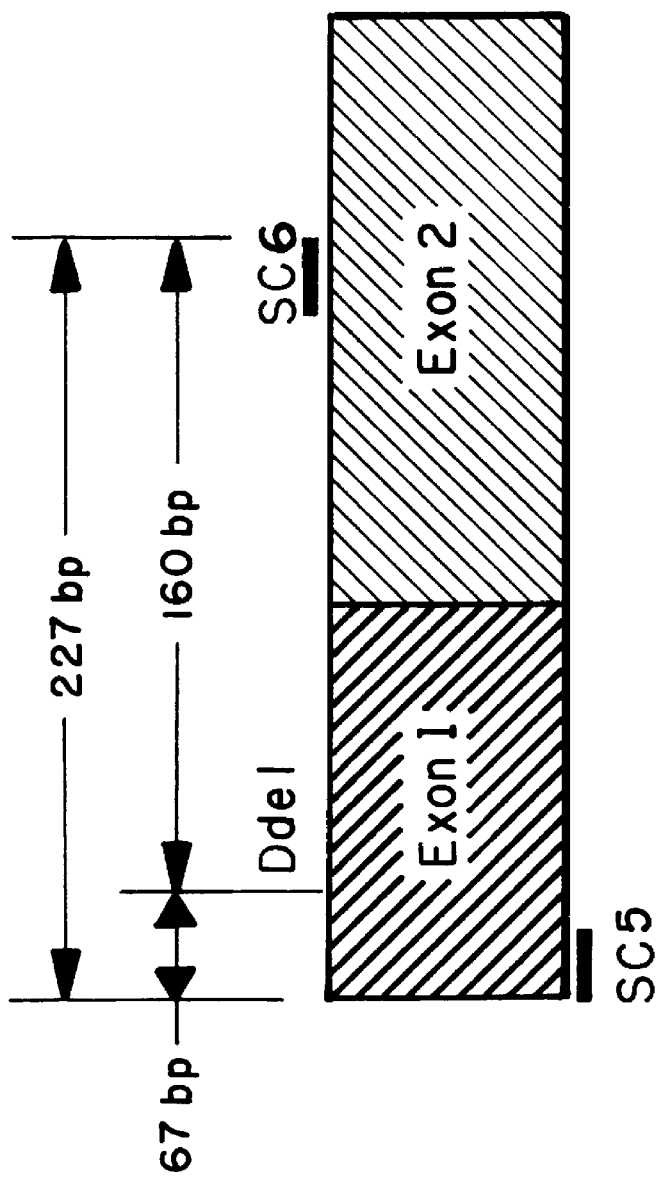
FIG. 8 is a schematic representation of the RT-PCR and Dde I restriction digestion analysis of β-globin mRNA-derived cDNA.

FIG. 8 shows PCR analysis of human β-globin DNA. Primers are listed in Table 3. FIG. 8 is a schematic representation of the RT-PCR and Dde I restriction digestion analysis of β-globin mRNA-derived cDNA.

The method and assay of the present invention are more specifically described in FIGS. 9–13.

FIGS. 9A–D shows fluorescent micrographs of allele-specific in situ RT-PCR of two, one normal and one mutated, cell lines.

FIGS. 9A–D show allele-specific in situ RT-PCR of a normal epithelial cell line (16HBE14o-) and a CF tracheal epithelial cell line homozygous for the ΔF508 mutation (ΣCFTE29o-). A primer pair specific for normal CFTR mRNA sequences (CF7B/CF22) seen in Tables 1 and 2 was used to assess wild-type CFTR expression in both cell lines. Primer CF7B is allele-specific for wtCFTR and primer CF22 is non-allele-specific in exon 11. The resultant amplification gives rise to a product that crosses intron-exon boundaries and therefore only amplifies mRNA-derived mutated CFTR cDNA. Amplifications were carried out in the presence of fluorescence labeled nucleotide precursors such as dUTP.

Figure 9A:
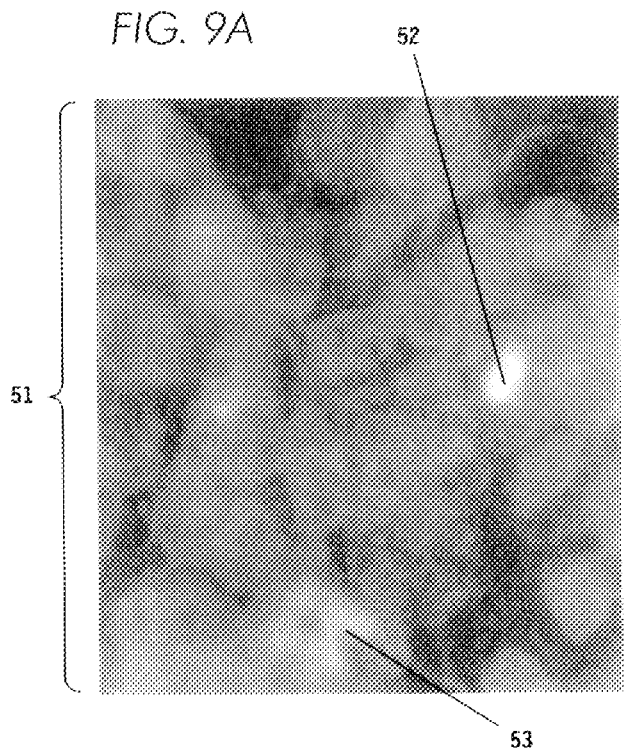
FIGS. 9A–9D are fluorescent micrographs of allele-specific in situ RT-PCR of cell lines.

FIG. 9A is in situ PCR of normal 16HBE14o- cells following DNase treatment and reverse transcription (+RT). In FIG. 9A, area 51 seen in the colored original has varying blue green colors. White areas 52 and 53 seen in the black and white FIG. 9A are yellow in the color original.

Figure 9B:

FIG. 9B is in situ RT-PCR of mutated ΣCFTE29o- cells. As seen in FIG. 9B, the wild-type CFTR DNA was not expressed in the mutated cells. On the colored photograph, there are no yellow areas or fluorescence observed. The FIG. 9B is virtually all blue.

Figure 9C:
Figure 9D:

FIG. 9C represents in situ PCR of 16HBE140-, and FIG. 9D represents in situ PCR of ΣCFTE29o- without reverse transcription (−RT). Because there was no reverse transcription performed in the studies showing FIGS. 9C and 9D, there is no yellow fluorescence observed in either of these figures. FIGS. 9B–D show some very slight green but the light areas are mostly blue seen as black in FIGS. 9B–D. Only FIG. 9A is positive for the presence of wtCFTR mRNA.

Figure 10:
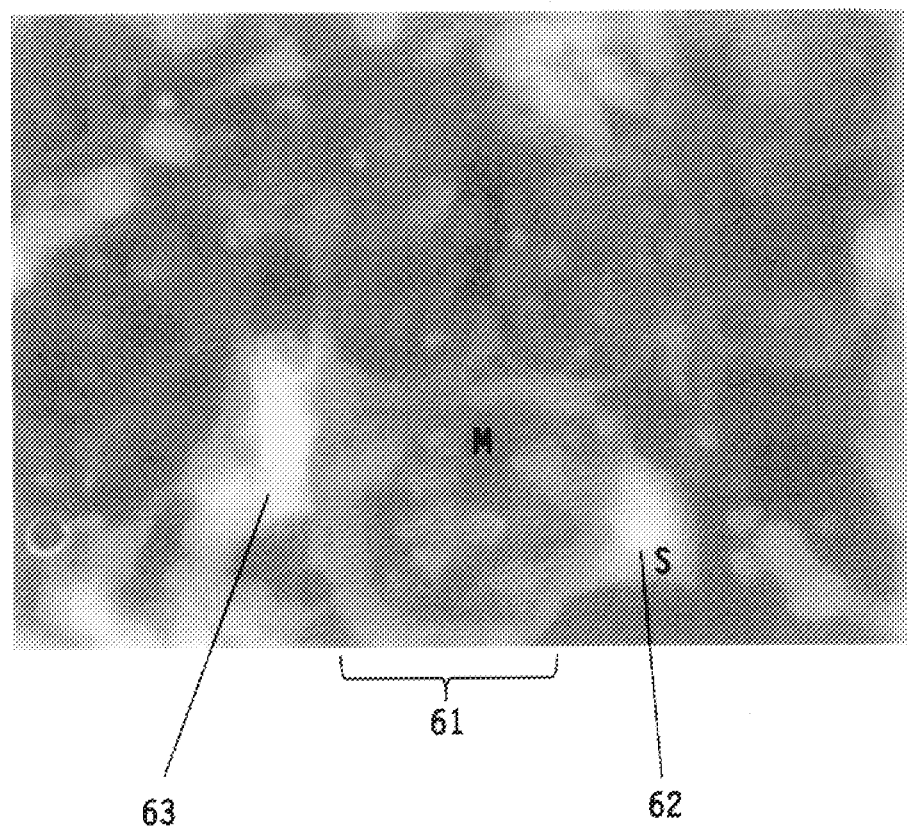
FIG. 10 is an fluorescent micrograph of cells which show allele-specific in situ RT-PCR of a section of normal bronchial epithelial tissue.

FIG. 10 is a color fluorescent photograph of cells submitted to human allele-specific in situ RT-PCR of a section normal bronchial epithelial tissue. Mucous (M) cells and serous (S) cells are indicated.

In FIG. 10, the light areas 62 and 63 which are yellow in the original are for serous cells, and areas 61 are blue green for mucous. RT-PCR was carried out as described above for FIGS. 9A–D. Fluorescence was observed primarily in serous cells and only to a smaller degree in the mucous cells. Results indicate the presence of wtCFTR mRNA predominantly in serous cells and not in mucous cells.

Using a wtPCR primer pair, specific for wtCFTR expression, studies were carried out on both cultured cells (FIGS. 9A–D) and tissue sections (FIG. 10). The results show expression of wtCFTR in normal cells. No ΔF508 expression was detected in ΔF508 homozygote CF cells using this primer pair (FIGS. 9A–D). In tissue sections, wtCFTR expression appears to be confined primarily to serous cells (FIG. 10).

The method of detection employs polymerase chain reaction (PCR) amplification of mRNA-derived cDNA. The primers used in are allele-specific and will differentiate between the endogenous mutant (ΔF508) cystic fibrosis transmembrane conductance regulator (CFTR) genes and therapeutic wild-type CFTR DNA. One primer is non-allele-specific and in an exon adjacent to the exon containing the mutation and one primer is specific for either ΔF508 or wild-type CFTR. Effectively 3 primers are necessary for this analysis.

The results of several other studies are seen in the FIGS. 11–13. The studies represent analysis of the expression of specific CFTR alleles (ΔF508 and wild-type) in cells and tissue sections. Expression of CFTR in cells was determined using PCR primers that differentiate between the wt and ΔF508 CFTR alleles.

FIG. 11 is allele-specific in situ RT-PCR in human tissue showing assessment of wtCFTR in sections of human airway epithelial tissue.

FIG. 11A shows wtCFTR mRNA detected in normal bronchial tissue with primers CF17/CF7C (upper panel), but not with the ΔF508 primers CF17/CF8C (lower panel). On colored micrograph, the yellow fluorescence is visible over the whole photograph in upper panel. Lower panel shows only traces of the fluorescence, seen as small white spots. Wild-type CFTR was primarily expressed and the expression detected in the submucosal glands in serous cells (S) and not in mucous cells (M).

Expression was also detected in the lumen of the colon (FIG. 11B).

Figures 12A, 12B:
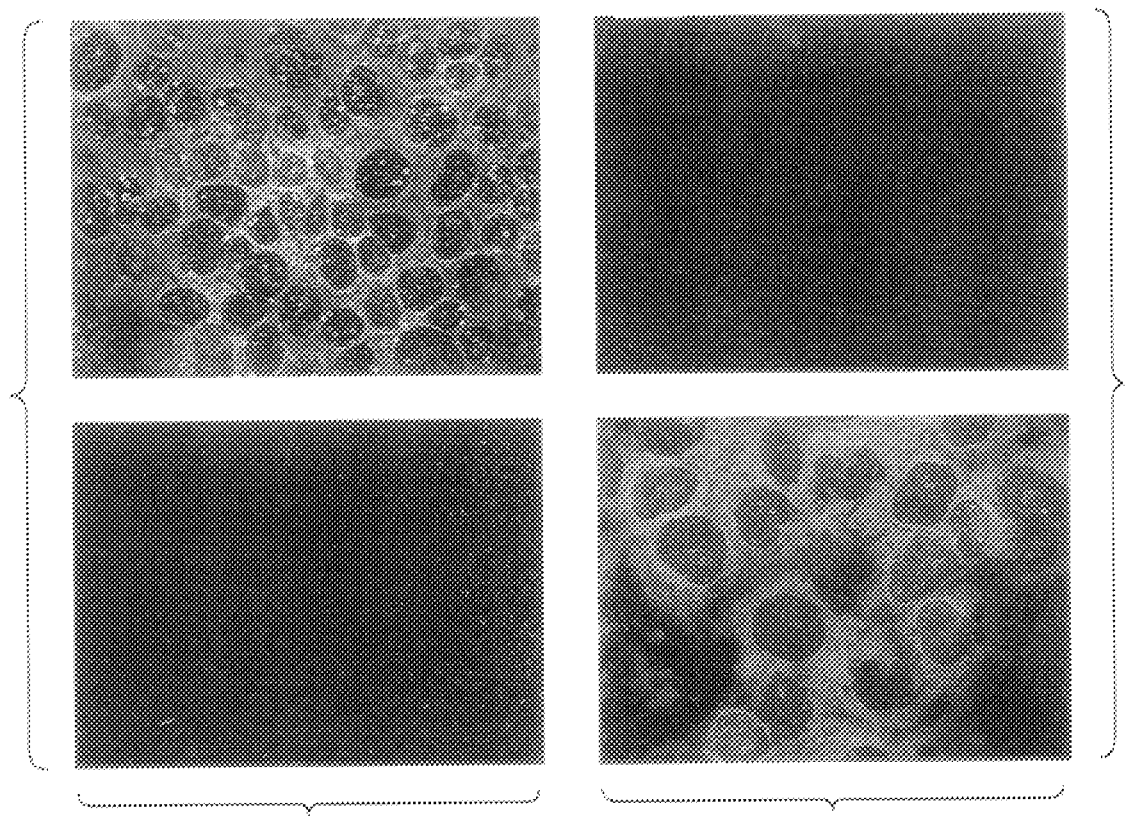
FIGS. 12A–C are allele-specific in situ RT-PCRs in human bronchial epithelial cell line.

FIG. 11B shows wtCFTR mRNA detected in normal human colon tissue with allele-specific primers CF17/CF7C for wt DNA (left top panel), but not with allele-specific primers CF17/CF8C to mutation (top right panel). Fluorescence was seen throughout the crypt, the lower part of microvillus where newer cells are found. Conventional in situ hybridization has shown CFTR mRNA in this region. In this Figure, the crypt shows the strongest signal as seen in the bottom panel. FIG. 12 is allele-specific in situ RT-PCR in human bronchial epithelial cell line. Analysis of cultured airway epielial cells shows that the primers were able to differentiate between the expression of wild-type and ΔF508 CFTR (FIGS. 12A and 12B). In studies looking at mixed populations of airway epithelial cells, i.e., CFBE41o- (ΔF/ΔF) and 16HBE14o- cells, it was possible to differentiate the wt 16HBE14o- from the ΔF/ΔF CFBE41o- cells (FIG. 12C).

FIG. 12A shows wild-type (wt) CFTR mRNA detected in normal bronchial epithelial cells (16HBE14o-) using a wt-specific oligonucleotide primer pair (CF17/CF7C), top panel. As seen in FIG. 12A bottom panel, no signal was detected with a ΔF508-specific oligonucleotide primer pair (CF17/CF8C).

FIG. 12B shows ΔF508 CFTR mRNA detected in CF bronchial epithelial cells (CFBE41o-) that were homozygous for the ΔF508 mutation when the ΔF508-specific primer pair was used, (FIG. 12B, bottom panel). No signal was detected when primers specific for the wt-allele were used (FIG. 12B, top panel).

Figure 12C:
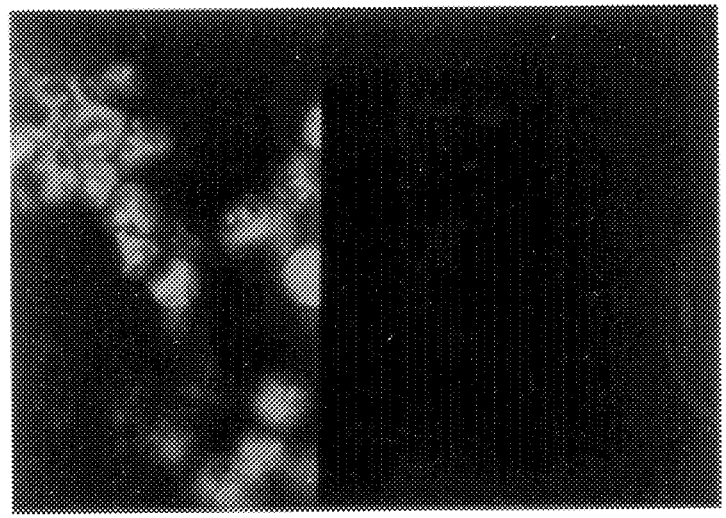

FIG. 12C shows a mixed population of 16HBE14o- and ΣCFBE41o- cells where it was possible to identify those cells expressing the wtCFTR allele with primers CF17/CF7C. The left panel was with reverse transcription (+RT) where some green fluorescence is visible. The right panel, which shows samples which were not reverse transcribed, does not show visible fluorescence (−RT).

Further studies were carried out in vivo using the SFHR approach. Normal mice were transfected with liposome-DNA complexes by intralung instillation. DNA fragments were comprised of mouse CFTR (mCFTR) exon 10 and flanking intron 9 and 10 DNA sequences. The entire fragment was 783-bp and contained a ΔF508 mutation (a TTT deletion of codon 508) and a silent mutation (T>C) to give rise to a unique Kpn I restriction enzyme cleavage site. The expression of this exogenous sequence was assayed as RNA from tissue harvested 4 days after the mice were transfected. Tissue was harvested from the trachea, lungs and the liver. Extraction of the RNA occurred immediately after the tissue was removed from the animal. The RNA was then reverse transcribed and first strand cDNA was amplified by allele-specific PCR with primers mCF12r and mCFΔF508-3. Results are seen in FIG. 13.

Figure 13A:
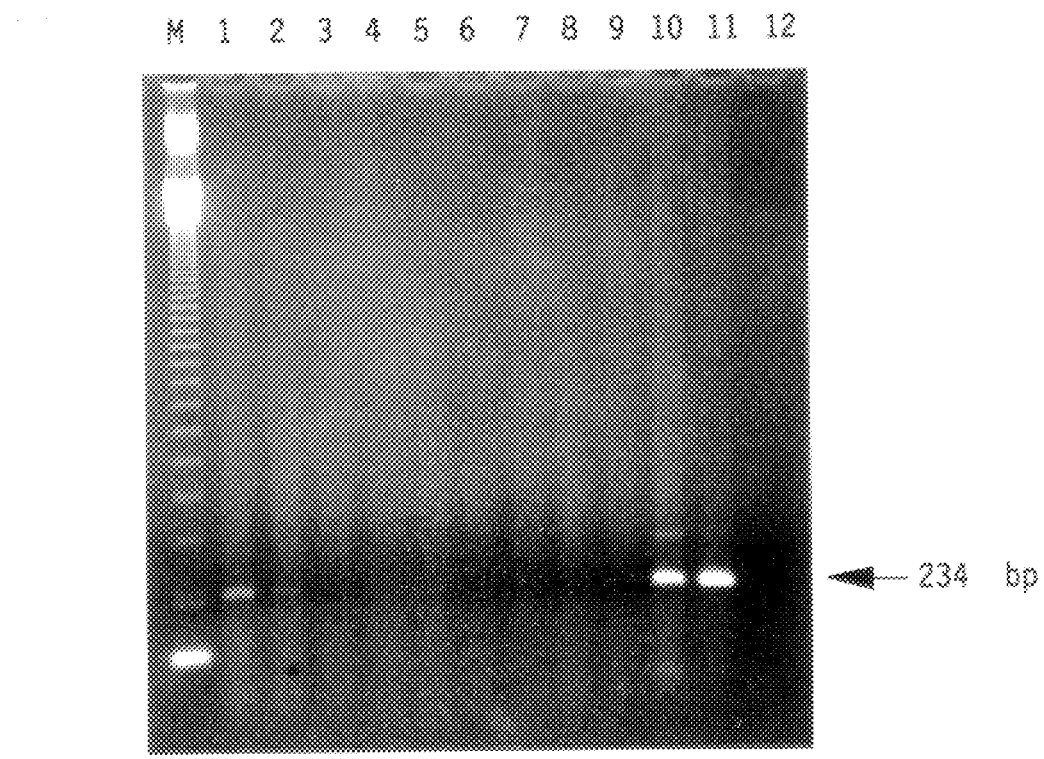
FIGS. 13A–B shows allele-specific RT-PCRs analysis of RNA samples isolated from transfected mice at day 4 post-transection in various organs transfected or nontransfected (FIG. 13A) and Kpn 1 Restriction enzyme cleavage (FIG. 13B).
Figure 13B:
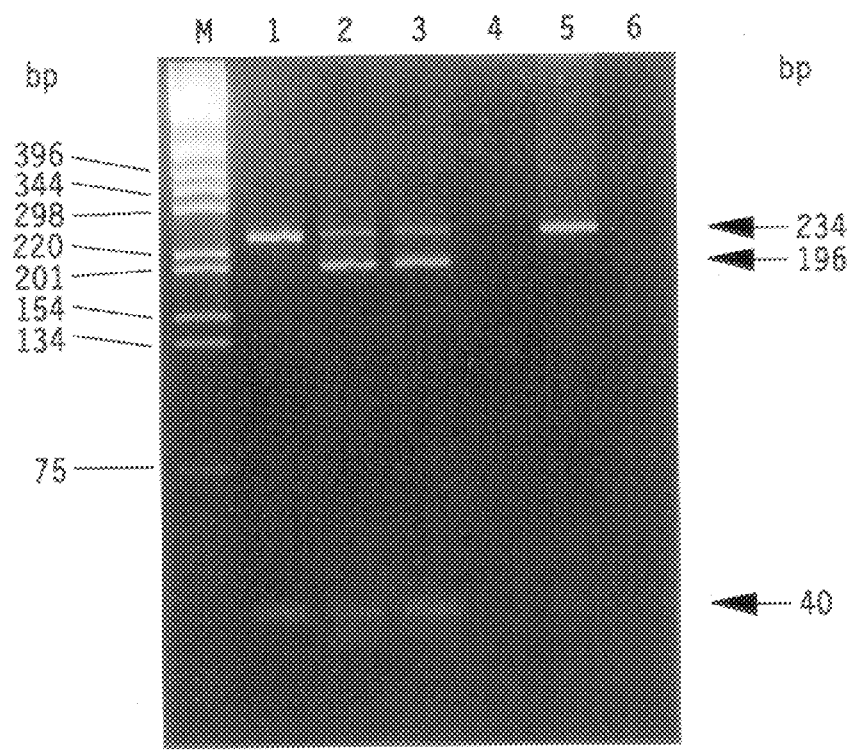

FIG. 13 is allele-specific RT-PCR analysis of RNA samples isolated from transfected mice at day 4 post-transfection. FIG. 13A lanes 1–3 show lung, lanes 4–6 show trachea, lanes 7–9 show heart tissue. Lanes 1, 4, and 7 were transfected with 4 µg of DNA. Lanes 2, 5 and 8 were transfected with 20 µg DNA. Lanes 3, 6 and 9 were controls without DNA transfection. Lanes 10 (liver) and 11 (lung) are positive controls for allele-specific RT-PCR from heterozygous ΔF508 mouse samples. Lane 12 is water control. The molecular weight marker is a 123-bp ladder. FIG. 13B shows Kpn 1 restriction enzyme cleavage of a second round PCR amplification product from lanes 1 and 2 (FIG. 13A). Lane 1 shows lung sample from mice transfected with 4 µg DNA without Kpn 1 digestion. Lanes 2 and 3 Kpn 1 show digest of PCR products from mice transfected with 4 and 20 µg, respectively. Lane 4 shows nontransfected control amplification and Kpn 1 digest. Lane 5 shows Kpn 1 digest of PCR product from a ΔF508 heterozygote control mouse; and lane 6, shows water control. The marker (lane M) is a 1-kb molecular weight marker (Gibco BRL). The results of the initial amplification indicated that there was, in fact, ΔF508 CFTR mRNA expressed in the lung tissue (FIG. 13A). After a second round of amplification, the fragment was digested with Kpn 1. After electrophoreses on a 4% NuSiev agarose gel, digestion with Kpn 1 was confirmed (FIG. 13B).

These results indicate that SFHR occurs in vivo and that it is useful for altering specific sequences in somatic cells and that the SFHR is successfully detected using assay method and the primers of the invention.

UTILITY

The assay of the invention is used to quantify the number of cells within a population of CF cells transfected in vitro or in vivo expressing wt CFTR.

The development of this method and assay to determine success of a particular gene therapy protocol is important for defining which gene therapy protocol will be the best for given disease or target organ. It is important to differentiate between the expression of endogenous mutant sequences and the exogenous wild-type correcting DNA (whether the therapeutic DNA in the form of cDNA or DNA fragments).

The approach that has been developed and described herein involves allele-specific detection of expressed genes. The disease on which the assay and method of the invention was confirmed has been cystic fibrosis, however, this technique has general application to a number of other disease states. In addition, this technique is also important for analysis of the developmental effects of the expression of specific alleles as well as the diagnostic assessment of the expression of mutant alleles involved in cancer.

In a more preferred embodiment, the method of the invention is applied to the alteration of the genetic defects associated with CF disease. However, the method is suitable and applicable to cells with other genetic defects for which the wild-type or otherwise normal DNA sequence is known. Also within this invention is the detection of alterations of DNA sequences associated with genetic diseases in animals other than humans. These detectable genetic diseases can either be induced as in the case of transgenic animals, or they can be corrected as in the case of gene therapy.

The current invention is useful for verification and assessment of gene therapy used for correction of genetic disorders. While the invention was proven to work for cystic fibrosis, almost all genetic diseases can be detected according to the invention.

It will be apparent to a person skilled in the art that this assay and a method also provides a means for verification of altering DNA sequences which do not express a gene product, including alterations in regulatory sequences, intron sequences, and the substitution of redundant codon sequences.

EXAMPLE 1

Preparation of the Wild-type 491 Base Pair DNA and Primers

This example illustrates preparation of the wt 491 bp DNA and primers.

The 491 bp fragment was generated using the T6/20 plasmid described in *Science*, 245:1059–1065(1989), (ATCC, NJ). The identity of the plasmid was verified by restriction enzyme mapping and further amplified as previously described. After digestion with Eco RI and Hind III, an 860 bp DNA was separated following electrophoresis in 0.8% Seaplaque agarose gel. The fragment obtained contained exon 10 as well as 5' and 3' intron sequences as verified by the restriction enzyme cleavage (*Genomics*, 10:214–228(1991)). A 50 ng aliquot of the DNA fragment was amplified by the polymerase chain reaction (PCR) according to U.S. Pat. No. 4,965,188, using primers CF1 and CF5.

The amplified fragment was analyzed on a 1% agarose gel, and then amplified in bulk in 20 separate PCR amplifications each containing 50 ng. The 491 bp fragments were purified by phenol:chloroform:isoamyl alcohol (25:24:1) extraction, and precipitated with 100% ethanol at −70° C. for 30 min. The DNA was centrifuged in an Eppendorf microcentrifuge at 14,000 rpm, for 10 min at 40° C. The pellet was washed once with 70% ethanol and then with 100% ethanol. After drying, the DNA was resuspended in dd $H_2O$ at a concentration of 1 µg/µl.

Primers and probes were prepared on automated DNA Synthesizers (Models 390B and 394, Applied Biosystems, Foster City, Calif.).

The sequences of the primers and probes were selected from the CFTR gene sequence published in *Genomics*, 10: 214–228 (1991). The sequences of the DNA and RNA primers are shown in Tables 1–6.

EXAMPLE 2

PCR Conditions for Solution Amplification

This example describes condition used for amplification of primers by PCR.

The PCR conditions for individual primers are as follows:
CF6/CF7/8 (404/407 bp fragment)
  1:500 dilution of DNA from CF1/CF6 amplification, 1/µM primers, 0.8 mM $Mg^{+2}$.
  Cycle: denaturation 94° C. for 30 sec, annealing 49° C. for 20 sec extension 72° C. for 20 sec with a 4 sec/cycle increase in extension time for 35 cycles.
CF17/22 (470 bp fragment CFTR gene 1338–1811),
CF17/oligo N/oligo ΔF
  DNA amplified from 1 µg RNA (35 cycles), 1 µM primer, 1.5 mM $Mg^{+2}$.
  Cycle: denaturation 94° C. for 1 min, annealing 51° C. for 1 min extension 72° C. for 20 sec with a 4 sec/cycle increase in extension time for 40 cycles.
CF7B/CF6 and CF8B/CF6 414- and 411-bp fragments, respectively;

Primers, 0.5 μM; DNA, 50–100 ng;
Cycle: denaturation 95° C. for 60 s, annealing 56° C. for 60 s, 72° C. for 120 s; 35 cycles with an 8 min extension on the last cycle; and $Mg^{+2}$ mM.

CF1B/CF7C (N) and CF1B/CF8C (ΔF) 392- and 389-bp fragments, respectively.

Conditions were as follows:
Primers, 0.5 μM;DNA, 50–100 ng;
Cycle: denaturation 95° C. for 60 s, annealing 59° C. for 60 s, 72° C. for 90 s; 35 cycles with an 8 min extension on the last cycle; and $Mg^{+2}$ 2 mM.

CF17/CF7C–8C: 330-bp (N) AND 327-bp (ΔF),
Primers, 1 μM;
Cycle: denaturation 94° C. for 30 s; annealing, 57° C. for 30 s; extension, 72° C. for 30 s for 35 cycles with a 5 min extension on the last cycle; and $Mg^{+2}$, 2.0 mM.

SC5/SC6: 357-bp (DNA PCR) 227-bp (RT-PCR),
Primers, 5 μM;
Cycle: denaturation 94° C. for 20 s; annealing, 58° C. for 60 s; extension, 72° C. for 60 s for 35 cycles with a with a 5 min extension on the last cycle; and $Mg^{+2}$, 2.5 mM.

CF17/CF22: 470-bp (ΔF) and 473-bp (N) fragments.
Conditions were as follows:
Primers, 0.5 μM; DNA, 5–100 ng;
Cycle: denaturation 94° C. for 30 s, annealing 56° C. for 30 s, 72° C. for 30 s; 30 cycles with an 8 min extension on the last cycle; and $mg^{+2}$ mM.

Mouse primers:
mCF508-3/mCF11R:
Cycle: denaturation 94° C. for 20s annealing, 58° C. for 20 s, 72° C. for 30 s, for 35 cycles.
mCF12R/mCF11R:
Cycle: denaturation 94° C. for 20 s, annealing 58° C. for 20 s, 72° C. for 30 s for 35 cycles.
mCFN-3/mCF11R:
Cycle: denaturation 94° C. for 20 s, annealing 58° C. for 20 s, 72° C. for 30 s, for 35 cycles.

EXAMPLE 3

Hybridization of Probes to Filters Extrapolate to in situ Conditions

This example illustrates the conditions for hybridization of probes to filters to extrapolate to in situ conditions.

DNA fragments were separated by agarose gel electrophoresis. The gels with the fragments were incubated in 0.4N NaOH containing 0.6M NaCl for 30 min to denature DNA and then washed one time with 1.5M NaCl, 0.5M Tris-HCl for 30 min.

The DNA was transferred to a Gene Screen Plus membrane (NEN-Dupont) by capillary blot and again denatured with 0.4N NaOH for 1 min followed by neutralization with 0.2M Tris-HCl. The membranes were prehybridized for 1 hour at 37° C. in 6xSSC, 5xDenhardt's, 1% SDS, and 100 μg/ml of denatured salmon sperm DNA.

The oligonucleotide probes (oligo N or oligo ΔF; 10 ng) were radiolabelled by reaction with 20 units of T4 kinase and 40 μCi $^{32}$P-γ-ATP for 30 min at 37° C. Unincorporated nucleotides were removed by centrifugation of the reaction mix through a minispin column.

Hybridization was carried out overnight at 37° C., the membranes were washed 2 times for 5 min each in 2xSSC at room temperature, 2 times for 30 min in 2xSSC, 0.1% SDS at 45° C., and 1 time in 0.1xSSC for 30 min at room temperature. Autoradiographic emulsion was applied to the membranes after washing.

EXAMPLE 4

Reverse Transcriptase And Polymerase Chain Reaction (RT-PCR)

This example illustrates reverse transcriptase polymerase chain reaction procedure used in detection of SFHR in cystic fibrosis.

Human bronchial cells and cystic fibrosis human tracheal epithelial cells, grown to 70% confluence, were trypsinized, washed in PBS, resuspended in PBS, and cytospins made on Superfrostplus slides (Fisher). Cells were fixed in 4% PFA 2–4 hours or overnight, and dehydrated in 70% ethanol/DEPC water. Slides are stored at –80° C. until use. Before use, slides were placed in 55° C. oven for 10–30 minutes to help bind cells tightly to the slide. Cells were digested with trypsin (0.05%), or pronase (10 μg/ml), for a varying amount of time which was dependent on length of time of fixation—about 10–20 minutes. Slides were washed in DEPC water and were then dehydrated.

Cells were treated with DNase(1 u/μl) overnight at 37° C. and washed. One of two sections treated with DNase was reverse transcribed in 50 μl solution per sample containing Perkin Elmer solutions, 1x RT buffer, 1 mM DTT, 1 mM of each nucleotide, 2 μl random primers, 2.5 μl RNasin, and 1 μl reverse transcriptase. A parafilm coverslip was added, and the solution was placed in a humid chamber at 42° C. for 45 min. The resulting product was washed with PBS.

The PCR reaction was performed again using Perkin Elmer solutions containing a 50 μl final volume: 1x PCR buffer II, 700 μM each nucleotide, 10 μM each primer, 4.5 mM $MgCl_2$, 70 μM fluorescently labelled d-UTP, and 10 units of Taq (is) DNA polymerase. A hotstart was performed with the in situ PCR system 1000, thermal cycler, 25 cycles, target temperature, 59° C.

EXAMPLE 5

Procedure For RT-PCR

This example describes RT-PCR procedure used for detection of DNA expressions in various tissues.

Human airway epithetial cells were grown to ~70% confluence according to *PNAS*, 88: 5951–5955 (1988) and *Cell Mol. Biol.* 10: 38–47 (1994), trypsinized, washed and resuspended in PBS. Cells were either cytospun onto slides (in situ PCR Glass Slides, Perkin Elmer) or added to the slides fropwise and allowed to air dry. The cells were fixed with 4% paraformaldehyde (PFA) for 2–4 and then dried after dipping in 70% ethanol: diethylpyrocarbonate (DPEC) water.

Tissues, either lung, bronchial or colon cells, were fixed for 4 h in paranormal-dehyde fixative PFA followed by incubation of 30% sucrose in PBS overnight. Tissue sections were frozen in Octanol using Freon and liquid nitrogen. Slides were then stored at –70° C. until used. Before use, slides were placed in a 55° C. oven for 10–30 minutes to help bind the cells tightly to the slides. Cells and tissue were then digested with pepsin (2 mg/ml), for varying periods of time (15–45 min) that were dependent on the fixation time. The slides were washed 1x with 1x PBS and 70% ethanol and then air dried.

DNase digestion of each tissue run in 3 sections (1 U/μl or 10 U/section in NaAc, pH 5.0, 5 mM $MgSO_4$) was carried out overnight at 37° C. and followed by a wash and a dehydration step. Sections 1 and 2 were treated with DNase and 1 of 3 sections were reverse transcribed. Reaction volumes (50 μl) were composed of 1× Perkin Elmer reverse transcriptase (RT) buffer containing 1 mM DTT, 1 mM each dNTP, 1 μM antisense primer, 2500 U/ml M-MuLV, or Superscript II, (BRL) 2000 U/ml. A parafilm was used to cover the slides and the reaction was carried out at 42° C. for 45 min in a humidified chamber. The slides were washed 1× with 1× PBS and 70% ethanol and then air dried.

The PCR reaction was carried out in a 50 μl volume with 1× PCR buffer II (Perkin Elmer): 200 μM each dNTP, 10 μM each primer, 4.5 mM MgCl$_2$, 10 μM fluorescein labeled dUTP (Boerhringer Mannheim), and 10 U/section Taq (Is) DNA polymerase. PCR amplification was performed following a hot start (70° C. for 5–10 min, then 94° C. for 2 min) with the Perkin Elmer in situ PCR System 1000 Therma Cycler. The Cycle conditions were: 94° C./60 s, denaturation; 59° C./2 min, annealing; 70° C./60 s, extension for 20 cycles.

EXAMPLE 6

Assay for Detection of Allele-Specific Mutation and Verification of Their Replacement with Wild-Type DNA Fragments This example describes the assay used for differentiation between gene expression in tested tissue or cells and gene expression in the normal wild-type tissue or cells.

The assay comprises the following steps:
(a) obtaining tissue samples as follows:
  (1) a sample of the tested tissue or cells of the individual to be tested for genetic disease or from the individual previously submitted to gene therapy; and
  (2) a sample of the normal control tissue or cells of the same type or a wild-type DNA corresponding to the same healthy tissue to serve as a control;
(b) fixing, digesting and reverse transcribing both samples (1) and (2) of step (a) using procedures described in Examples 4 and 5, on separate slides, each slide containing three drops or sections of the same tissue or cells to ensure the correct interpretation, each drop to be treated as follows:
  (1) one drop (experimental or tested) is submitted to DNase digestion to expose single strand mRNA to be used as a template for production of cDNA and also to eliminate tissue or cells own DNA and prevent false positive results from this DNA, and subsequently this drop is submitted to reverse transcription to produce first strand cDNA from the mRNA template;
  (2) one drop serving as a negative control is submitted to DNase digestion but is not reverse transcribed and should show no staining;
  (3) one drop serving as a positive control is only submitted to reverse transcription but not to DNase digestion, and should show strong staining in the nucleus;
(c) amplifying the cDNA of step (b) using polymerase chain reaction in the presence of the allele-specific primers for wild-type DNA or tested experimental and/or mutated DNA, depending on what is being tested, under conditions and in a solution comprising all necessary nucleotides to obtain the cDNA in sufficient quantity for assay, wherein at least one nucleotide in the solution or in the primer is labelled with a non-interfering radioactive, immunochemical, fluorescent or other labeled marker detectable by spectroscopic, autoradiographic, immunocytochemical or enzymatic detection means;
(e) detecting the presence of the labeled marker in the amplified product which detects either the mutated DNA or the wild-type DNA, depending on the allele-specific primers used for PCR amplification, by detecting the presence and quantity of expression of mutated or normal wild-type DNA in the tested sample and/or in the control sample; and
(f) comparing qualitatively and quantitatively the results obtained in step (e), for tested and control samples wherein the presence of the labeled nucleotide in the amplified product using wild-type allele-specific primers determines the expression of the normal nonmutated DNA and wherein the absence of the labeled nucleotide in the amplified product using mutated allele-specific primers determines the absence of the expression of the mutated allele, and wherein the amount or the level of the labeled nucleotide can be quantified and the number of expressions of the mutated allele vis-a-vis expressions of the wild-type DNA determined by, for example using NIH image program or by any other means suitable for quantification.

Allele-specific primers and conditions used for PCR amplification are described in the specification and in Example 2.

EXAMPLE 7

The Assay for Detection of Various Genetic Diseases and for Qualitative and Quantitative Assessment of the Gene Therapy Success This example illustrates an assay used for detection of various genetic diseases and for qualitative and quantitative assessment of the gene therapy success or for designing the gene therapy protocol. Genetic diseases for which this assay is suitable are selected from the group consisting of cystic fibrosis, Fanconi's anemia, sickle cell anemia, retinitis pigmentosa, xeroderma pigmentosa, ataxia telangiectasia, Bloom's syndrome, retinoblastoma, Duchenne's muscular dystrophy, and Tay-Sachs disease.

In the assay described in Example 6, the endogenous tissue or cells are obtained from individuals suffering from, suspected to be suffering from or having the family history of cystic fibrosis or from the individual subjected to gene therapy by replacing the cystic fibrosis transmembrane conductive regulator (CFTR) gene with wild-type nonmutated DNA.

In the assay described in Example 6, the endogenous tissue or cells are obtained from individual suffering from sickle cell anemia.

In the assay described in Example 6, the endogenous tissue or cells are obtained from individual suffering from xeroderma pigmentosa.

In the assay described in Example 6, the endogenous tissue or cells are obtained from individual suffering from genetic disease listed above.

EXAMPLE 8

The Assay for Detection of Precancerous Cells and for qualitative and quantitative Assessment of the Gene Therapy This example illustrates an assay used for detection of precancerous conditions in the cells having the normal phenotype.

The assay as described in Example 6 is used for detection of cancerous mutations in the cells as well as for designing the suitable protocol for gene therapy by replacing the mutated DNA within the cells with nonmutated DNA and for verification that such replacement did, in fact happened.

In the assay described in Example 6, the endogenous tissue or cells suspected to carry the cancer mutations are obtained and the presence or the absence of the mutations is confirmed by using the assay of the Example 6.

What is claimed is:

1. An assay for qualitative and quantitative detection of expression of a mutated or nonmutated human cystic fibrosis gene in a tissue or cells of a human subject to be tested, the assay comprising the steps:
    (a) obtaining:
        (1) a sample of the tissue or cells of a human subject to be tested for cystic fibrosis or from a human subject previously subjected to gene therapy for cystic fibrosis; and
        (2) a sample of nonmutated control tissue cells or wild-type DNA corresponding to the same type of nonmutated tissue to serve as a control;
    (b) fixing, digesting and reverse transcribing the samples obtained in step (a) to obtain cDNA;
    (c) amplifying the cDNA obtained in step (b) using polymerase chain reaction in the presence of allele-specific primers or allele-nonspecific primers selected from the group of primers identified as SEQ ID NOS: 1–15 and SEO ID NOS: 32–46, under conditions and in a solution comprising all necessary nucleotides to obtain the cDNA in sufficient quantity for assay, wherein at least one nucleotide in the solution or in the primers is labeled with a non-interfering radioactive, immunocytochemical, fluorescent or other labeled marker detectable by spectroscopic, autoradiographic, immunocytochemical or enzymatic detection means;
    (d) detecting the presence and quantity of cystic fibrosis gene expression in the samples obtained in step (a) by detecting the presence and quantity of the labeled marker of step (c) in the amplified cDNA; and
    (e) comparing qualitatively and quantitatively the results obtained in step (d)
    wherein the absence of the labeled marker in the cDNA amplified with mutated allele-specific primers, or wherein the presence of the labeled marker in the cDNA amplified with wild-type allele-specific primers, indicates the detection of a nonmutated cystic fibrosis gene; and
    wherein the presence of the labeled marker in the cDNA amplified with mutated allele-specific primers, or wherein the absence of the labeled marker in the cDNA amplified with wild-type allele-specific primers, indicates the detection of a mutated cystic fibrosis gene.

2. The assay of claim 1 wherein the amount or the level of the labeled marker is quantified by counting the number of cells containing the labeled marker.

3. A method for detection of allele-specific mutations of the human cystic fibrosis gene in a human subject by an assay for detection of and differentiation between expression of a mutated cystic fibrosis gene and expression of a nonmutated cystic fibrosis gene in a human subject, said method comprising steps:
    (a) obtaining a sample of tissue or cells from a human subject to be tested for mutations in the cystic fibrosis gene;
    (b) obtaining a control sample of cells of the same tissue or cell type as the tissue or cells of step (a) or a sample of nonmutated wild-type DNA from a healthy human subject;
    (c) fixing the cells obtained in steps (a) and step (b);
    (d) digesting the cells fixed in step (c) to expose the single stranded mRNA and to eliminate DNA contained in the cells;
    (e) subjecting the mRNA exposed in step (d) to reverse transcription to obtain first-strand complementary DNA(cDNA);

(f) subjecting the cDNA obtained in step (e) to polymerase chain reaction amplification to obtain the cDNA in sufficient quantity for a detection and differentiation assay, said amplification performed in the presence of allele-specific or allele-nonspecific primers selected form the group of primers identified as SEQ ID NOS: 1–15 and SEQ ID NOS: 32–46, using a solution comprising at least one non-interfering labeled nucleotide marker detectable by spectroscopic, autoradiographic, immunocytochemical or enzymatic detection means;

(g) detecting the presence and quantity of cystic fibrosis gene expression in the samples obtained in step (a) and step (b) by detecting the presence and quantity of the labeled marker of step (f) in the amplified cDNA; and (h) comparing qualitatively and quantitatively the results obtained in step (g) wherein the absence of the labeled marker in the cDNA amplified with mutated allele-specific primers, or wherein the presence of the labeled marker in the cDNA amplified with wild-type allele-specific primers, indicates the detection of a nonmutated cystic fibrosis gene; and wherein the presence of the labeled marker in the cDNA amplified with mutated allele-specific primers, or wherein the absence of the labeled marker in the cDNA amplified with wild-type allele-specific primers, indicates the detection of a mutated cystic fibrosis gene.

4. The method of claim 3 wherein the control sample is the wild-type DNA.

5. The method of claim 3 wherein the sample of step (a) is a bioptic tissue sample from the human subject to be tested.

6. The assay of claim 3 wherein the primers are allele-specific.

7. The assay of claim 3 wherein the primers are allele-nonspecific.

8. A method for assessment of success of a gene therapy for correction of a mutated cystic fibrosis gene in a human subject subjected to the gene therapy by an assay for detection of and differentiation between expression of a mutated cystic fibrosis gene and expression of a nonmutated cystic fibrosis gene in a human subject, said method comprising steps:

(a) obtaining a sample of cells from the human subject subjected to the gene therapy for correction of a mutated cystic fibrosis gene;

(b) obtaining a control sample of cells of the same tissue type as the cells obtained in step (a) or a sample of nonmutated wild-type cells from a healthy human subject;

(c) fixing the cells obtained in step (a) and step (b);

(d) digesting the cells fixed in step (c) to expose the single stranded mRNA and to eliminate DNA contained in the cells;

(e) subjecting the mRNA exposed in step (d) to reverse transcription to obtain first-strand complementary DNA(cDNA);

(f) subjecting the cDNA obtained in step (e) to polymerase chain reaction amplification to obtain the cDNA in sufficient quantity for a detection and differentiation assay, said amplification performed in the presence of wild-type or mutated allele-specific or allele-nonspecific primers selected from the group of primers identified as SEQ ID NOS: 1–15 and SEQ ID NOS: 32–46, using a solution comprising at least one non-interfering labeled nucleotide marker detectable by spectroscopic, autoradiographic, immunocytochemical or enzymatic detection means;

(g) detecting the presence and quantity of cystic fibrosis gene expression in the sample of cells obtained in step (a) and step (b) by detecting the presence and quantity of the labeled marker of step (f) in the amplified cDNA; and (h) evaluating qualitatively and quantitatively the results obtained in step (g) wherein the absence of the labeled marker in the cDNA amplified with mutated allele-specific primers, or wherein the presence of the labeled marker in the cDNA amplified with wild-type allele-specific primers, obtained from the human subject subjected to the gene therapy, confirms the correction of the cystic fibrosis gene and success of the gene therapy; and wherein the presence of the labeled marker in the cDNA amplified with mutated allele-specific primers, or wherein the absence of the labeled marker in the cDNA amplified with wild-type allele-specific primers, obtained from the human subject subjected to the gene therapy, represents unsuccessful gene therapy.

9. The method of claim 8 wherein the sample obtained in step (a) is a bioptic tissue sample obtained from the human subject subjected to gene therapy.

* * * * *